(12) United States Patent
Desenne et al.

(10) Patent No.: US 7,153,331 B2
(45) Date of Patent: Dec. 26, 2006

(54) DYEING COMPOSITION FOR KERATINOUS FIBERS COMPRISING AN OXYETHYLENE RAPESEED FATTY ACID AMIDE

(75) Inventors: Patricia Desenne, Bois Collombes (FR); Cécile Bebot, Clichy (FR); Florence Laurent, Bois Colombes (FR)

(73) Assignee: L'Oreal S.A. (FR)

( * ) Notice: Subject to any disclaimer, the term of this patent is extended or adjusted under 35 U.S.C. 154(b) by 0 days.

(21) Appl. No.: 10/499,021

(22) PCT Filed: Dec. 20, 2002

(86) PCT No.: PCT/FR02/04519

§ 371 (c)(1),
(2), (4) Date: Feb. 22, 2005

(87) PCT Pub. No.: WO03/053329

PCT Pub. Date: Jul. 3, 2003

(65) Prior Publication Data

US 2005/0125912 A1   Jun. 16, 2005

(30) Foreign Application Priority Data

Dec. 21, 2001 (FR) .................................. 01 16745

(51) Int. Cl.
*A61K 7/13* (2006.01)
(52) U.S. Cl. .................... 8/405; 8/406; 8/410; 8/411; 8/421; 8/435; 8/586
(58) Field of Classification Search .................. 8/405, 8/406, 586, 410, 411, 421, 435
See application file for complete search history.

(56) References Cited

U.S. PATENT DOCUMENTS

| | | | |
|---|---|---|---|
| 2,261,002 A | 10/1941 | Ritter | 260/570 |
| 2,271,378 A | 1/1942 | Searle | 167/22 |
| 2,273,780 A | 2/1942 | Dittmar | 260/28 |
| 2,375,853 A | 5/1945 | Kirby et al. | 260/583 |
| 2,388,614 A | 11/1945 | Kirby et al. | 167/23 |
| 2,454,547 A | 11/1948 | Bock et al. | 256/587.6 |
| 2,961,347 A | 11/1960 | Floyd | 117/141 |
| 3,206,462 A | 9/1965 | McCarty | 260/256.4 |
| 3,227,615 A | 1/1966 | Korden | 167/87.1 |
| 3,472,840 A | 10/1969 | Stone et al. | 260/231 |
| 3,632,559 A | 1/1972 | Matter et al. | 260/78 |
| 3,836,537 A | 9/1974 | Boerwinkle et al. | 260/29.6 |
| 3,874,870 A | 4/1975 | Green et al. | 71/67 |
| 3,912,808 A | 10/1975 | Sokol | 424/71 |
| 3,915,921 A | 10/1975 | Schlatzer, Jr. et al. | 260/17.4 |
| 3,917,817 A | 11/1975 | Vanlerberghe et al. | 424/70 |
| 3,929,990 A | 12/1975 | Green et al. | 424/78 |
| 3,966,904 A | 6/1976 | Green et al. | 424/78 |
| 3,986,825 A | 10/1976 | Sokol | 81/10.2 |
| 4,001,432 A | 1/1977 | Green et al. | 424/329 |
| 4,003,699 A | 1/1977 | Rose et al. | 8/10.2 |
| 4,005,193 A | 1/1977 | Green et al. | 424/168 |
| 4,013,787 A | 3/1977 | Vanlerberghe et al. | 424/70 |
| 4,025,617 A | 5/1977 | Green et al. | 424/78 |
| 4,025,627 A | 5/1977 | Green et al. | 424/248.4 |
| 4,025,653 A | 5/1977 | Green et al. | 424/325 |
| 4,026,945 A | 5/1977 | Green et al. | 260/567.6 |
| 4,027,008 A | 5/1977 | Sokol | 424/62 |
| 4,027,020 A | 5/1977 | Green et al. | 424/248.56 |
| 4,031,307 A | 6/1977 | DeMartino et al. | 536/114 |
| 4,068,035 A | 1/1978 | Violland et al. | 428/279 |
| 4,131,576 A | 12/1978 | Iovine et al. | 260/17.4 |
| 4,157,388 A | 6/1979 | Christiansen | 424/70 |
| 4,165,367 A | 8/1979 | Chakrabarti | 424/47 |
| 4,168,144 A | 9/1979 | Curry et al. | 8/10.1 |
| 4,172,887 A | 10/1979 | Vanlerberghe et al. | 424/70 |
| RE30,199 E | 1/1980 | Rose et al. | 8/10.2 |
| 4,189,468 A | 2/1980 | Vanlerberghe et al. | 424/70 |
| 4,197,865 A | 4/1980 | Jacquet et al. | 132/7 |
| 4,217,914 A | 8/1980 | Jacquet et al. | 132/7 |
| 4,223,009 A | 9/1980 | Chakrabarti | 424/47 |
| 4,240,450 A | 12/1980 | Grollier et al. | 132/7 |
| 4,277,581 A | 7/1981 | Vanlerberghe et al. | 525/420 |
| 4,349,532 A | 9/1982 | Vanlerberghe et al. | 424/47 |
| 4,381,919 A | 5/1983 | Jacquet et al. | 8/405 |
| 4,422,853 A | 12/1983 | Jacquet et al. | 8/406 |
| 4,445,521 A | 5/1984 | Grollier et al. | 132/7 |
| 4,509,949 A | 4/1985 | Huang et al. | 586/558 |
| 4,591,610 A | 5/1986 | Grollier | 524/55 |
| 4,608,250 A | 8/1986 | Jacquet et al. | 424/71 |
| 4,702,906 A | 10/1987 | Jacquet et al. | 424/70 |

(Continued)

FOREIGN PATENT DOCUMENTS

DE    23 59 399 A1    6/1975

(Continued)

OTHER PUBLICATIONS

Porter, M. R.; "Handbook of Surfactants;" 1991; pp. 116-178; Blackie & Son (Glasgow and London); 1991.

(Continued)

*Primary Examiner*—Eisa Elhilo
(74) *Attorney, Agent, or Firm*—Finnegan, Henderson, Farabow, Garrett & Dunner L.L.P.

(57) ABSTRACT

The invention relates to a composition for the oxidation dyeing of keratin fibers, in particular human keratin fibers and more particularly the hair, comprising, in a medium that is suitable for dyeing, at least one oxidation dye, characterized in that it comprises more than 5% by weight of the composition of at least one oxyethylenated rapeseed fatty acid amide.

The invention also relates to the dyeing processes and devices using the said composition.

46 Claims, No Drawings

U.S. PATENT DOCUMENTS

| | | | |
|---|---|---|---|
| 4,719,099 A * | 1/1988 | Grollier et al. | 424/47 |
| 4,719,282 A | 1/1988 | Nadolsky et al. | 528/310 |
| 4,725,282 A | 2/1988 | Hoch et al. | 8/408 |
| 4,761,273 A | 8/1988 | Grollier et al. | 424/47 |
| 4,839,166 A | 6/1989 | Grollier et al. | 424/71 |
| 4,948,579 A | 8/1990 | Jacquet et al. | 424/72 |
| 4,996,059 A | 2/1991 | Grollier et al. | 424/71 |
| 5,009,880 A | 4/1991 | Grollier et al. | 424/47 |
| 5,061,289 A | 10/1991 | Clausen et al. | 8/405 |
| 5,089,252 A | 2/1992 | Grollier et al. | 424/47 |
| 5,124,079 A | 6/1992 | Smid et al. | 252/548 |
| 5,139,037 A | 8/1992 | Grollier et al. | 132/203 |
| 5,196,189 A | 3/1993 | Jacquet et al. | 424/72 |
| 5,380,340 A | 1/1995 | Neunhoeffer et al. | 8/409 |
| 5,534,267 A | 7/1996 | Neunhoeffer et al. | 424/701 |
| 5,663,366 A | 9/1997 | Neunhoeffer et al. | 548/371.4 |
| 5,766,576 A | 6/1998 | Löwe et al. | 424/62 |
| 5,879,412 A | 3/1999 | Rondeau et al. | 8/411 |
| 5,958,392 A | 9/1999 | Grollier et al. | 424/70.17 |
| 6,099,592 A | 8/2000 | Vidal et al. | 8/409 |
| 6,099,593 A | 8/2000 | Terranova et al. | 8/409 |
| 6,284,003 B1 | 9/2001 | Rose et al. | 8/412 |
| 6,338,741 B1 | 1/2002 | Vidal et al. | 8/409 |
| 6,432,146 B1 | 8/2002 | Rondeau | 8/407 |
| 6,470,847 B1 | 10/2002 | Kawamoto | 132/196 R |
| 6,530,959 B1 | 3/2003 | Lang et al. | 8/405 |
| 6,645,258 B1 | 11/2003 | Vidal et al. | 8/405 |
| 6,695,887 B1 | 2/2004 | Cottard et al. | 8/405 |
| 6,939,537 B1 | 9/2005 | Ohta et al. | |
| 2001/0015190 A1 | 8/2001 | Kawamoto | 132/196 |
| 2001/0023515 A1 | 9/2001 | Cottard et al. | 8/406 |
| 2002/0010970 A1 | 1/2002 | Cottard et al. | 438/622 |
| 2002/0050013 A1 | 5/2002 | Vidal et al. | 8/405 |
| 2001/0184717 | 12/2002 | Cottard et al. | 8/405 |
| 2003/0019051 A9 | 1/2003 | Vidal et al. | 8/405 |
| 2003/0074747 A1* | 4/2003 | Vuarier et al. | 8/405 |
| 2003/0086897 A1 | 5/2003 | Ohta et al. | |
| 2003/0124079 A1 | 7/2003 | Mougin et al. | 424/70.11 |
| 2003/0172474 A1 | 9/2003 | Lang et al. | 8/405 |
| 2004/0141943 A1 | 7/2004 | Mougin et al. | 424/70.17 |
| 2004/0205901 A1 | 10/2004 | Cottard et al. | 8/405 |
| 2005/0071933 A1 | 4/2005 | Rondeau | 8/405 |
| 2005/0196367 A1 | 9/2005 | Ohta et al. | |

FOREIGN PATENT DOCUMENTS

| | | |
|---|---|---|
| DE | 38 43 892 A1 | 6/1990 |
| DE | 41 33 957 A1 | 4/1993 |
| DE | 195 43 988 A1 | 5/1997 |
| EP | 0 080 976 B1 | 9/1986 |
| EP | 0 122 324 B1 | 1/1988 |
| EP | 0 166 100 B1 | 1/1989 |
| EP | 0 173 109 B1 | 10/1989 |
| EP | 0 216 479 B1 | 2/1991 |
| EP | 0 337 354 B1 | 2/1994 |
| EP | 0 386 826 B1 | 5/1994 |
| EP | 1 025 834 A1 | 8/2000 |
| FR | 1 400 366 | 5/1965 |
| FR | 1 492 597 | 9/1966 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 A1 | 11/1987 |
| FR | 2 733 749 A1 | 11/1996 |
| FR | 2 750 048 | 12/1997 |
| FR | 2 782 450 A1 | 2/2000 |
| FR | 2 782 451 A1 | 2/2000 |
| FR | 2 782 452 A1 | 2/2000 |
| FR | 2 811 993 A1 | 1/2002 |
| FR | 2 820 032 | 8/2002 |
| GB | 1 026 978 | 4/1966 |
| GB | 1 153 196 | 5/1969 |
| JP | 49-050145 A | 5/1974 |
| JP | 2-19576 | 1/1990 |
| JP | 8-337560 A | 12/1996 |
| JP | 9-020740 A | 1/1997 |
| JP | 9-110659 | 4/1997 |
| JP | 2000-239132 A | 9/2000 |
| JP | 2001-206829 A | 7/2001 |
| JP | 2001-213737 | 7/2001 |
| JP | 2001-220330 A | 8/2001 |
| JP | 2001-234747 A | 8/2001 |
| WO | WO 94/08969 | 4/1994 |
| WO | WO 94/08970 | 4/1994 |
| WO | WO 96/15765 | 5/1996 |
| WO | WO 98/44012 | 10/1998 |
| WO | WO 00/68282 | 11/2000 |
| WO | WO 03/053329 A2 | 7/2003 |

OTHER PUBLICATIONS

Fonnum, G. et al.; "Associative thickners. Part I: synthesis, Rheology and Aggregation Behavior;" *Colloid Polymer Science.*; vol. 271; pp. 380-389; 1993.
International Search Report of PCT/FR 02/04519 (present application).
English Language Derwent Abstract for DE 195 43 988 A1.
English Language Derwent Abstract for DE 41 33 957 A1.
English Language Derwent Abstract for DE 38 43 892 A1.
English Language Derwent Abstract for DE 23 59 399 A1.
English Language Derwent Abstract for EP 1 025 834 A1.
English Language Derwent Abstract for EP 0 166 100 B1.
English Language Derwent Abstract for EP 0 080 976 B1.
English Language Derwent Abstract for FR 2 820 032.
English Language Derwent Abstract for FR 2 811 993 A1.
English Language Derwent Abstract for FR 2 782 452 A1.
English Language Derwent Abstract for FR 2 782 451 A1.
English Language Derwent Abstract for FR 2 782 450 A1.
English Language Derwent Abstract for FR 2 782 048.
English Language Derwent Abstract for FR 2 733 749 A1.
English Language Derwent Abstract for FR 2 598 611 A1.
English Language Derwent Abstract for FR 2 542 997.
English Language Derwent Abstract for FR 2 519 863.
English Language Derwent Abstract for FR 2 505 348.
English Language Derwent Abstract for FR 2 470 596.
English Language Derwent Abstract for FR 2 413 907.
English Language Derwent Abstract for FR 2 393 573.
English Language Derwent Abstract for FR 2 383 660.
English Language Derwent Abstract for FR 2 368 508.
English Language Derwent Abstract for FR 2 336 434.
English Language Derwent Abstract for FR 2 320 330.
English Language Derwent Abstract for FR 2 316 271.
English Language Derwent Abstract for FR 2 280 361.
English Language Derwent Abstract for FR 2 270 846.
English Language Derwent Abstract for FR 2 252 840.
English Language Derwent Abstract for FR 2 190 406.
English Language Derwent Abstract for FR 2 162 025.
English Language Derwent Abstract for FR 2 080 759.

English Language Derwent Abstract for FR 2 077 143.
English Language Derwent Abstract for FR 1 583 363.
English Language Derwent Abstract for FR 1 400 366.
English Language Derwent Abstract for JP 2001-234747 A.
English Language Derwent Abstract for JP 2001-220330 A.
English Language Derwent Abstract for JP 2001-206829 A.
English Language Derwent Abstract for JP 2000-239132 A.
English Language Derwent Abstract for JP 9-020740 A.
English Language Derwent Abstract for JP 8-337560 A.
English Language Derwent Abstract for JP 9-1-10659.
English Language Derwent Abstract for JP 2-19576.
English Language Derwent Abstract for JP 9-050145 A.

\* cited by examiner

DYEING COMPOSITION FOR KERATINOUS FIBERS COMPRISING AN OXYETHYLENE RAPESEED FATTY ACID AMIDE

The present invention relates to a composition for the oxidation dyeing of keratin fibres, in particular human keratin fibres and more particularly the hair, comprising, in a medium that is suitable for dyeing, at least one oxidation dye and also at least one oxyethylenated rapeseed fatty acid amide.

The invention also relates to the processes and devices using the said composition.

It is known practice to dye keratin fibres, and in particular human hair, with dye compositions containing oxidation dye precursors, generally known as "oxidation bases", in particular ortho- or para-phenylenediamines, ortho- or para-aminophenols, and heterocyclic bases.

Oxidation dye precursors are compounds that are initially uncoloured or only weakly coloured, which develop their dyeing power on the hair in the presence of oxidizing agents, leading to the formation of coloured compounds. The formation of these coloured compounds results either from an oxidative condensation of the "oxidation bases" with themselves or from an oxidative condensation of the "oxidation bases" with coloration modifiers, or "couplers", which are generally present in the dye compositions used in oxidation dyeing and are represented more particularly by meta-phenylenediamines, meta-aminophenols and meta-diphenols, and certain heterocyclic compounds.

The variety of molecules used, which consist on the one hand of the "oxidation bases" and on the other hand of the "couplers", allows a very wide range of colours to be obtained.

These oxidation bases and these couplers are formed in vehicles or supports that allow them to be applied to the keratin fibres after mixing with an oxidizing agent.

These vehicles are generally aqueous and, in order for the dye composition not to run down the face during the leave-in time, they generally contain a thickener.

Thus, to obtain oxidation dye compositions that are easy to apply to the hair without running beyond the areas that it is intended to dye, use has been made in the past of fatty acid amides, especially coconut fatty acid amides such as coconut acid diethanolamide or coconut acid monoisopropanolamide, or an alkyl ether carboxylic acid monoethanolamide oxyethylenated with 2 mol of ethylene oxide.

These fatty acid amides produce oxidation dye compositions that have very good rheological qualities, but that nevertheless could be further improved.

After considerable research conducted in this matter, it has been found, entirely surprisingly and unexpectedly, that it is possible to obtain oxidation dye compositions whose application conditions are improved relative to the compositions of the prior art by using an oxyethylenated rapeseed fatty acid amide in a certain content.

Oxidation dye compositions comprising an oxyethylenated rapeseed fatty acid amide thus have rheological behaviour that is significantly more satisfactory than those of the prior art with other fatty acid amides (increased viscosity and/or stability), especially after mixing with the oxidizing composition.

They also allow strong and chromatic shades to be obtained, with good fastness.

One subject of the present invention is thus a composition for the oxidation dyeing of keratin fibres, in particular human keratin fibres and more particularly the hair, comprising, in a medium that is suitable for dyeing, at least one oxidation dye, and also comprising more than 5% by weight of the composition of at least one oxyethylenated rapeseed fatty acid amide.

Another subject of the invention relates to a ready-to-use composition for the oxidation dyeing of keratin fibres, which comprises, in a medium that is suitable for dyeing, at least one composition as described above and at least one oxidizing agent.

For the purposes of the present invention, the expression "ready-to-use composition" means the composition intended to be applied in unmodified form to the keratin fibres, i.e. it may be stored in unmodified form before use, or may result from the extemporaneous mixing of two or more compositions.

The invention is also directed towards a process for the oxidation dyeing of keratin fibres, and in particular human keratin fibres such as the hair, consisting in applying to the fibres a dye composition comprising, in a medium that is suitable for dyeing, at least one oxidation dye and more than 5% by weight of the composition of at least one oxyethylenated rapeseed fatty acid amide, the colour being developed at alkaline, neutral or acidic pH using an oxidizing composition comprising, in a medium that is suitable for dyeing, at least one oxidizing agent, which is mixed just at the time of use with the dye composition or which is applied sequentially without intermediate rinsing.

A subject of the invention is also a multi-compartment dyeing device or "kit" for the oxidation dyeing of keratin fibres, in particular of human keratin fibres and more particularly the hair, which comprises one compartment containing a dye composition comprising, in a medium that is suitable for dyeing, at least one oxidation dye and more than 5% by weight of the composition of at least one oxyethylenated rapeseed fatty acid amide, and another compartment containing an oxidizing composition comprising, in a medium that is suitable for dyeing, an oxidizing agent.

However, other characteristics, aspects, subjects and advantages of the invention will emerge even more clearly on reading the description and the examples that follow.

The oxyethylenated rapeseed fatty acid amides that may be used according to the present invention more particularly comprise, on average, 1 to 20 mol of ethylene oxide, preferably 1 to 10 mol of ethylene oxide and more particularly 1 to 5 mol of ethylene oxide.

Advantageously, the amide corresponds to the following formula:

$$RCONH(CH_2CH_2O)nH,$$

in which R is derived from the fatty acid obtained from rapeseed, and n is a mean number between 1 and 20, preferably between 1 and 10 and more preferably between 1 and 5.

Among these amides, mention may be made of the commercial product Aminol® N sold by the company Chem Y, which is a rapeseed fatty acid amide comprising 4 mol of ethylene oxide.

As mentioned previously, the oxyethylenated rapeseed fatty acid amide(s) represent(s) more than 5% by weight of the composition.

According to one more particular variant of the invention, the content of oxyethylenated rapeseed fatty acid amide represents at least 5.5% by weight, more particularly at least 6% by weight of the composition.

Moreover, the content of oxyethylenated rapeseed fatty acid amide represents up to 20% by weight of the composition and preferably is less than 10% by weight of the composition. It should be noted that the composition does not contain the oxidizing agent.

Oxidation Dyes

The oxidation dyes that may be used according to the invention are chosen from oxidation bases and/or couplers.

Preferably, the compositions according to the invention contain at least one oxidation base.

The oxidation bases that may be used in the context of the present invention are chosen from those conventionally known in oxidation dyeing, and among which mention may be made in particular of the ortho- and para-phenylenediamines, double bases, ortho- and para-aminophenols and heterocyclic bases below, and also the addition salts thereof with an acid.

Mention may be made in particular of:

(I) the para-phenylenediamines of formula (I) below, and the addition salts thereof with an acid:

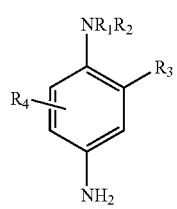

(I)

in which:

$R_1$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical or a $C_1$–$C_4$ alkyl radical substituted with a nitrogenous, phenyl or 4'-aminophenyl group;

$R_2$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical or a $C_1$–$C_4$ alkyl radical substituted with a nitrogenous group;

$R_1$ and $R_2$ may also form, with the nitrogen atom that bears them, a 5- or 6-membered nitrogenous heterocycle optionally substituted with one or more alkyl, hydroxyl or ureido groups;

$R_3$ represents a hydrogen atom, a halogen atom such as a chlorine atom, a $C_1$–$C_4$ alkyl radical, a sulfo radical, a carboxy radical, a $C_1$–$C_4$ monohydroxyalkyl radical, a $C_1$–$C_4$ hydroxyalkoxy radical, an acetylamino$(C_1$–$C_4)$alkoxy radical, a mesylamino$(C_1$–$C_4)$alkoxy radical or a carbamoylamino$(C_1$–$C_4)$alkoxy radical, $R_4$ represents a hydrogen or halogen atom or a $C_1$–$C_4$ alkyl radical.

Among the nitrogenous groups of formula (I) above, mention may be made in particular of amino, mono$(C_1$–$C_4)$alkylamino, di$(C_1$–$C_4)$alkylamino, tri$(C_1$–$C_4)$alkylamino, monohydroxy$(C_1$–$C_4)$alkylamino, imidazolinium and ammonium radicals.

Among the para-phenylenediamines of formula (I) above, mention may be made more particularly of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxy-ethyl-para-phenylenediamine and N-(4-aminophenyl)-3-hydroxypyrrolidine, and the addition salts thereof with an acid.

Among the para-phenylenediamines of formula (I) above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the addition salts thereof with an acid are most particularly preferred.

(II) According to the invention, the term double bases is understood to refer to compounds containing at least two aromatic nuclei bearing amino and/or hydroxyl groups.

Among the double bases that may be used as oxidation bases in the dye compositions in accordance with the invention, mention may be made in particular of the compounds corresponding to formula (II) below, and the addition salts thereof with an acid:

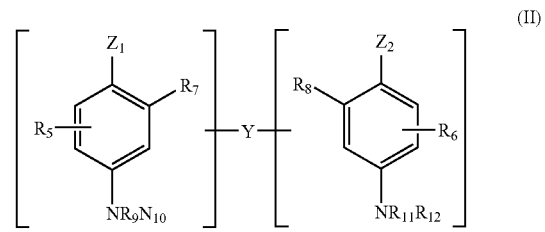

(II)

in which:

$Z_1$ and $Z_2$, which may be identical or different, represent a hydroxyl or —$NH_2$ radical which may be substituted with a $C_1$–$C_4$ alkyl radical or with a linker arm Y;

the linker arm Y represents a linear or branched alkylene chain containing from 1 to 14 carbon atoms, which may be interrupted by or terminated with one or more nitrogenous groups and/or one or more hetero atoms such as oxygen, sulfur or nitrogen atoms, and optionally substituted with one or more hydroxyl or $C_1$–$C_6$ alkoxy radicals;

$R_5$ and $R_6$ represent a hydrogen or halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical or a linker arm Y;

$R_7$, $R_8$, $R_9$, $R_{10}$, $R_{11}$ and $R_{12}$, which may be identical or different, represent a hydrogen atom, a linker arm Y or a $C_1$–$C_4$ alkyl radical; it being understood that the compounds of formula (II) contain only one linker arm Y per molecule.

Among the nitrogenous groups of formula (II) above, mention may be made in particular of amino, mono$(C_1$–$C_4)$ alkylamino, di(C$_1$–C$_4$)alkylamino, tri (C$_1$–C$_4$)alkylamino, monohydroxy(C$_1$–C$_4$)alkylamino, imidazolinium and ammonium radicals.

Among the double bases of formula (II) above, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl) tetramethylenediamine, N,N'-bis(4-methylaminophenyl) tetramethylenediamine, N,N'-bis (ethyl)-N,N'-bis(4'-amino-3'-methylphenyl)ethylenediamine and 1,8-bis (2,5-diaminophenoxy)-3,5-dioxaoctane, and the addition salts thereof with an acid.

Among these double bases of formula (II), N,N'-bis(β-hydroxyethyl)-N,N'-bis(4'-aminophenyl)-1,3-diaminopropanol and 1,8-bis(2,5-diaminophenoxy)-3,5-dioxaoctane, or one of the addition salts thereof with an acid, are particularly preferred.

(III) The para-aminophenols corresponding to formula (III) below, and the addition salts thereof with an acid:

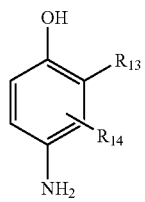

(III)

in which:

R$_{13}$ represents a hydrogen atom, a halogen atom, such as fluorine, or a C$_1$–C$_4$ alkyl, C$_1$–C$_4$ monohydroxyalkyl, (C$_1$–C$_4$)alkoxy(C$_1$–C$_4$)alkyl, C$_1$–C$_4$ aminoalkyl or hydroxy(C$_1$–C$_4$)alkylamino(C$_1$–C$_4$)alkyl radical, R$_{14}$ represents a hydrogen atom, a halogen atom, such as fluorine, or a C$_1$–C$_4$ alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or (C$_1$–C$_4$) alkoxy(C$_1$–C$_4$)alkyl radical.

Among the para-aminophenols of formula (III) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

(IV) The ortho-aminophenols that can be used as oxidation bases in the context of the present invention are chosen in particular from 2-aminophenol, 2-amino-1-hydroxy-5-methylbenzene, 2-amino-1-hydroxy-6-methylbenzene and 5-acetamido-2-aminophenol, and the addition salts thereof with an acid.

(V) Among the heterocyclic bases that may be used as oxidation bases in the dye compositions in accordance with the invention, mention may be made more particularly of pyridine derivatives, pyrimidine derivatives and pyrazole derivatives, and the addition salts thereof with an acid.

Among the pyridine derivatives, mention may be made more particularly of the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in German patent DE 2 359 399 or Japanese patents JP 88-169 571 and JP 91-10659 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl) amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine and 3-amino-5-methyl-7-imidazolylpropylaminopyrazolo[1,5-a]pyrimidine; and the addition salts thereof and the tautomeric forms thereof, when a tautomeric equilibrium exists, and the addition salts thereof with an acid.

Among the pyrazole derivatives, mention may be made more particularly of the compounds described in patents DE 3 843 892, DE 4 133 957 and patent applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylamino-pyrazole and 3,5-diamino-4-(β-hydroxyethyl) amino-1-methylpyrazole, and the addition salts thereof with an acid.

According to the present invention, the oxidation bases preferably represent from 0.0005% to 12% by weight approximately relative to the total weight of the composition (not including the oxidizing agent) and even more preferably from 0.005% to 8% by weight approximately relative to this weight.

The couplers that may be used in the dye composition according to the invention are those conventionally used in oxidation dye compositions, that is to say meta-aminophenols, meta-phenylenediamines, meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles and quinolines, and the addition salts thereof with an acid.

These couplers are chosen more particularly from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-β-hydroxyethylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, and the addition salts thereof with an acid.

When they are present, these couplers preferably represent from 0.0001% to 10% by weight approximately relative to the total weight of the composition (not including the oxidizing agent), and even more preferably from 0.005% to 5% by weight approximately.

In general, the addition salts with an acid of the oxidation bases and couplers are chosen in particular from the hydrochlorides, hydrobromides, sulfates, tartrates, lactates and acetates.

The dye composition in accordance with the invention may also comprise one or more direct dyes, especially to modify the shades by enriching them with glints. These direct dyes may be chosen especially from the neutral, cationic or anionic nitro dyes, azo dyes or anthraquinone dyes conventionally used or those described especially in patent applications FR-2 782 450, 2 782 451, 2 782 452 and EP-1 025 834, in a weight proportion of about from 0.001% to 20% and preferably from 0.01% to 10% of the total weight of the composition.

The dye composition in accordance with the invention may also comprise at least one surfactant of anionic, nonionic, cationic or amphoteric nature, in a proportion ranging from 0.01% to 40% and preferably from 0.1% to 30% by weight relative to the total weight of the composition.

Among the surfactants of anionic type, the ones that are preferably used according to the invention are weakly anionic surfactants, among which mention may be made more particularly of oxyalkylenated ether carboxylic acids and the salts thereof, having the formula (I) below:

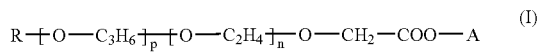

(I)

in which:
R represents a linear or branched $C_8$–$C_{22}$ alkyl or alkenyl radical or mixture of radicals, a ($C_8$–$C_9$)alkylphenyl radical or a radical R'CONH—$CH_2$—$CH_2$— with R' denoting a linear or branched $C_{11}$–$C_2$, alkyl or alkenyl radical,
n is an integer or fraction ranging from 2 to 24,
p is an integer or fraction ranging from 0 to 6,
A denotes a hydrogen atom or Na, K, Li, ½ Mg or a monoethanolamine, ammonium or triethanolamine residue.

The oxyalkylenated ether carboxylic acids or salts thereof preferably used according to the present invention are chosen from those of formula (I) in which R denotes a ($C_{12}$–$C_{14}$)alkyl, oleyl, cetyl or stearyl radical or mixture of radicals; a nonylphenyl or octylphenyl radical, A denotes a hydrogen or sodium atom, p=0, and n ranges from 2 to 20 and preferably from 2 to 10.

Compounds of formula (I) in which R denotes a ($C_{12}$) alkyl radical, A denotes a hydrogen or sodium atom, p=0 and n ranges from 2 to 10 are even more preferably used.

Among the commercial products that may preferably be used are the products sold by the company Chem Y under the names:
Akypo® NP 70 (R=nonylphenyl, n=7, p=0, A=H);
Akypo® NP 40 (R=nonylphenyl, n=4, p=0, A=H);
Akypo® OP 40 (R=octylphenyl, n=4, p=0, A=H);
Akypo® OP 80 (R=octylphenyl, n=8, p=0, A=H);
Akypo® OP 190 (R=octylphenyl, n=19, p=0, A=H);
Akypo® RLM 38 (R=($C_{12}$–$C_{14}$)alkyl, n=3.8, p=0, A=H);
Akypo® RLM 38 NV (R=($C_{12}$–$C_{14}$)alkyl, n=4, p=0, A=Na);
Akypo® RLM 45 (R=($C_{12}$–$C_{14}$)alkyl, n=4.5, p=0, A=H);
Akypo® RLM 45 NV (R=($C_{12}$–$C_{14}$)alkyl, n=4.5, p=0, A=Na);
Akypo® RLM 100 (R=($C_{12}$–$C_{14}$)alkyl, n=10, p=0, A=H);
Akypo® RLM 100 NV (R=($C_{12}$–$C_{14}$)alkyl, n=10, p=0, A=Na);
Akypo® RLM 130 (R=($C_{12}$–$C_{14}$)alkyl, n=13, p=0, A=H);
Akypo® RLM 160 NV (R=($C_{12}$–$C_{14}$)alkyl, n=16, p=0, A=Na);
Akypo® RO 20 (R=oleyl, n=2, p=0, A=H);
Akypo® RO 90 (R=oleyl, n=9, p=0, A=H);
Akypo® RCS 60 (R=cetyl/stearyl, n=6, p=0, A=H);
Akypo® RS 60 (R=stearyl, n=6, p=0, A=H);
Akypo® RS 100 (R=stearyl, n=10, p=0, A=H);
Akypo® RO 50 (R=oleyl, n=5, p=0, A=H), or by the company Sandoz under the names:
Sandopan ACA-48 (R=cetyl/stearyl, n=24, p=0, A=H);
Sandopan DTC-Acid (R=($C_{13}$) alkyl, n=6, p=0, A=H);
Sandopan DTC (R=($C_{13}$) alkyl, n=6, p=0, A=Na);
Sandopan LS 24 (R=($C_{12}$–$C_{14}$)alkyl, n=12, p=0, A=Na);
Sandopan JA 36 (R=($C_{13}$)alkyl, n=18, p=0, A=H), and more particularly the products sold under the following names:
Akypo® NP 70;
Akypo® NP 40;
Akypo® OP 40;
Akypo® OP 80;
Akypo® RLM 25;
Akypo® RLM 45;
Akypo® RLM 100;
Akypo® RO 20;
Akypo® RO 50;
Akypo® RLM 38.

The oxyalkylenated ether carboxylic acids or salts thereof represent from about 2% to 15% and preferably from about 3% to 10% of the total weight of the composition.

Among the nonionic surfactants, which are compounds that are well known per se (see in particular in this respect "Handbook of Surfactants" by M. R. Porter, published by Blackie & Son (Glasgow and London), 1991, pp. 116–178), mention may be made of (non-limiting list) polyethoxylated or polypropoxylated alkylphenols, alpha-diols or alcohols, having a fatty chain containing, for example, 8 to 22 carbon atoms, it being possible for the number of ethylene oxide or propylene oxide groups to range in particular from 1 to 50. Mention may also be made of copolymers of ethylene oxide and of propylene oxide, condensates of ethylene oxide and of propylene oxide with fatty alcohols; monoglycerolated or polyglycerolated fatty alcohols comprising an average 1 to 30 glycerol groups; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, and amine oxides such as $(C_{10}-C_{14})$alkylamine oxides or N-acylaminopropylmorpholine oxides.

According to the invention, it is preferred to use:
1) fatty alcohols containing from 8 to 22 carbon atoms and oxyethylenated with 1 to 10 mol of ethylene oxide. Among these, mention may be made more particularly of lauryl alcohol 2 EO, lauryl alcohol 3 EO, decyl alcohol 3 EO and decyl alcohol 5 EO;
2) monoglycerolated or polyglycerolated fatty alcohols, which may be represented by formula (II) below:

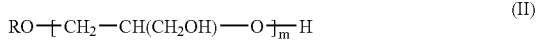

in which:

R represents a saturated or unsaturated, linear or branched radical containing from 8 to 40 carbon atoms and preferably from 10 to 30 carbon atoms;

m represents a number ranging from 1 to 30 and preferably from 1 to 10.

Compounds of this type that may be mentioned include lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The fatty alcohol may represent a mixture of fatty alcohols in the same respect that the value of m represents a random value, which means that several species of polyglycerolated fatty alcohols may coexist in a commercial product in the form of a mixture.

Among the mono- or polyglycerolated fatty alcohols that it is more particularly preferred to use are the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

The nonionic surfactant(s) represent(s) from 2% to 40% by weight approximately and preferably from 4% to 20% approximately of the total weight of the composition.

The ready-to-use composition according to the invention may also comprise in the dye composition and/or the oxidizing composition cationic or amphoteric polymers as described below and other rheology modifiers such as cellulose-based thickeners (hydroxyethylcellulose, hydroxypropylcellulose, carboxymethylcellulose, etc.), guar gum and its derivatives (hydroxypropyl guar, etc.), gums of microbial origin (xanthan gum, scleroglucan gum, etc.), crosslinked homopolymers of acrylic acid or of acrylamidopropanesulfonic acid and associative polymers as described below.

Preferentially, according to the invention, the colouring part comprises at least one cationic or amphoteric polymer and at least one associative polymer.

Cationic Polymers

For the purposes of the present invention, the expression "cationic polymer" denotes any polymer containing cationic groups and/or groups that may be ionized into cationic groups.

The cationic polymers that may be used in accordance with the present invention may be chosen from any of those already known per se as improving the cosmetic properties of the hair, namely, in particular, those described in patent application EP 337 354 and in French patents FR 2 270 846, 2 383 660, 2 598 611, 2 470 596 and 2 519 863.

The cationic polymers that are preferred are chosen from those containing units comprising primary, secondary, tertiary and/or quaternary amine groups, which may either form part of the main polymer chain or may be borne by a side substituent directly attached thereto.

The cationic polymers used generally have a number-average molecular mass of between 500 and $5 \times 10^6$ approximately and preferably between $10^3$ and $3 \times 10^6$ approximately.

Among the cationic polymers that may be mentioned more particularly are polymers of the polyamine, polyamino amide and polyquaternary ammonium type.

These are known products. They are described in particular in patents FR 2 505 348 and FR 2 542 997. Among the said polymers, mention may be made of:

(1) homopolymers or copolymers derived from acrylic or methacrylic esters or amides and comprising at least one of the units of formula (V), (VI), (VII) or (VIII) below:

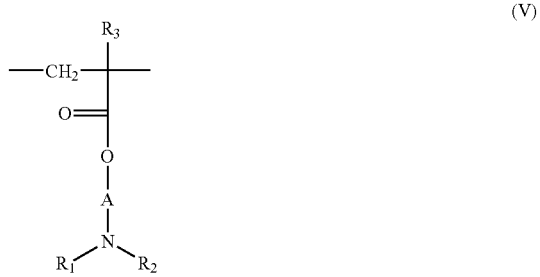

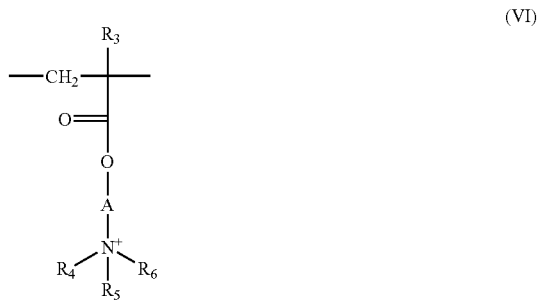

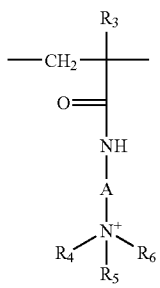

(VII)

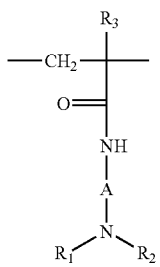

(VIII)

in which:
R$_3$, which may be identical or different, denote a hydrogen atom or a CH$_3$ radical;
A, which may be identical or different, represent a linear or branched alkyl group of 1 to 6 carbon atoms, preferably 2 or 3 carbon atoms, or a hydroxyalkyl group of 1 to 4 carbon atoms;
R$_4$, R$_5$ and R$_6$, which may be identical or different, represent an alkyl group containing from 1 to 18 carbon atoms or a benzyl radical and preferably an alkyl group containing from 1 to 6 carbon atoms;
R$_1$ and R$_2$, which may be identical or different, represent hydrogen or an alkyl group containing from 1 to 6 carbon atoms, and preferably methyl or ethyl;
X denotes an anion derived from an inorganic or organic acid, such as a methosulfate anion or a halide such as chloride or bromide.

The polymers of family (1) can also contain one or more units derived from comonomers that may be chosen from the family of acrylamides, methacrylamides, diacetoneacrylamides, acrylamides and methacrylamides substituted on the nitrogen with lower (C$_1$–C$_4$) alkyls, acrylic or methacrylic acids or esters thereof, vinyllactams such as vinylpyrrolidone or vinylcaprolactam, and vinyl esters.

Thus, among these polymers of family (1), mention may be made of:
copolymers of acrylamide and of dimethylaminoethyl methacrylate quaternized with dimethyl sulfate or with a dimethyl halide, such as the product sold under the name Hercofloc® by the company Hercules,
the copolymers of acrylamide and of methacryloyloxyethyltrimethylammonium chloride described, for example, in patent application EP-A-080 976 and sold under the name Bina Quat P 100® by the company Ciba Geigy,
the copolymer of acrylamide and of methacryloyloxyethyltrimethylammonium methosulfate sold under the name Reten® by the company Hercules,
quaternized or non-quaternized vinylpyrrolidone/dialkylaminoalkyl acrylate or methacrylate copolymers, such as the products sold under the name "Gafquat" ® by the company ISP, such as, for example, "Gafquat® 734" or "Gafquat® 755", or alternatively the products known as "Copolymer® 845, 958 and 937". These polymers are described in detail in patents FR 2 077 143 and FR 2 393 573,
dimethylaminoethyl methacrylate/vinylcaprolactam/vinylpyrrolidone terpolymers, such as the product sold under the name Gaffix VC® 713 by the company ISP,
vinylpyrrolidone/methacrylamidopropyldimethylamine copolymers sold in particular under the name Styleze® CC 10 by ISP, and
quaternized vinylpyrrolidone/dimethylaminopropylmethacrylamide copolymers such as the product sold under the name "Gafquat® HS 100" by the company ISP.

(2) The cellulose ether derivatives containing quaternary ammonium groups, described in French patent 1 492 597, and in particular the polymers sold under the names "JR®" (JR 400, JR 125 and JR 30M) or "LR®" (LR 400, or LR 30M) by the company Union Carbide Corporation. These polymers are also defined in the CTFA dictionary as quaternary ammoniums of hydroxyethylcellulose that has reacted with an epoxide substituted with a trimethylammonium group.

(3) Cationic cellulose derivatives such as cellulose copolymers or cellulose derivatives grafted with a water-soluble monomer of quaternary ammonium, and described in particular in U.S. Pat. No. 4,131,576, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.

The commercial products corresponding to this definition are more particularly the products sold under the names "Celquat® L 200" and "Celquat® H 100" by the company National Starch.

(4) The cationic polysaccharides described more particularly in U.S. Pat. Nos. 3,589,578 and 4,031,307, such as guar gums containing cationic trialkylammonium groups. Guar gums modified with a salt (e.g. chloride) of 2,3-epoxypropyltrimethylammonium are used, for example.

Such products are sold in particular under the trade names Jaguar® C13 S, Jaguar® C 15, Jaguar® C 17 or Jaguar® C162 by the company Meyhall.

(5) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, and also the oxidation and/or quaternization products of these polymers. Such polymers are described, in particular, in patents FR 2 162 025 and FR 2 280 361.

(6) Water-soluble polyamino amides prepared in particular by polycondensation of an acid compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound that is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, in particular, in patents FR 2 252 840 and FR 2 368 508.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical contains from 1 to 4 carbon atoms and preferably denotes methyl, ethyl or propyl. Such polymers are described in particular in patent FR 1 583 363.

Among these derivatives, mention may be made more particularly of the adipic acid/dimethylaminohydroxypropyl/diethylenetriamine polymers sold under the name "Cartaretine® F, F4 or F8" by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name "Hercosett® 57" by the company Hercules Inc. or alternatively under the name "PD 170®" or "Delsette® 101" by the company Hercules in the case of the adipic acid/epoxypropyl/diethylenetriamine copolymer.

(9) Cyclopolymers of alkyldiallylamine or of dialkyldiallylammonium, such as the homopolymers or copolymers containing, as main constituent of the chain, units corresponding to formula (IX) or (X):

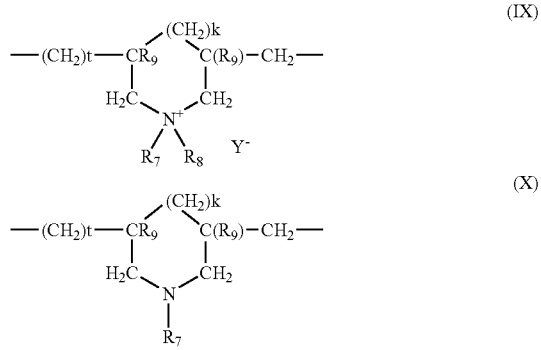

in which formulae k and t are equal to 0 or 1, the sum k+t being equal to 1; $R_9$ denotes a hydrogen atom or a methyl radical; $R_7$ and $R_8$, independently of each other, denote an alkyl group having from 1 to 6 carbon atoms, a hydroxyalkyl group in which the alkyl group preferably has 1 to 5 carbon atoms, a lower $C_1$–$C_4$ amidoalkyl group, or $R_7$ and $R_8$ can denote, together with the nitrogen atom to which they are attached, heterocyclic groups such as piperidyl or morpholinyl; $R_7$ and $R_8$, independently of each other, preferably denote an alkyl group having from 1 to 4 carbon atoms; $Y^-$ is an anion such as bromide, chloride, acetate, borate, citrate, tartrate, bisulfate, bisulfite, sulfate or phosphate. These polymers are described in particular in patent FR 2 080 759 and in its Certificate of Addition 2 190 406.

Among the polymers defined above, mention may be made more particularly of the dimethyldiallylammonium chloride homopolymer sold under the name "Merquat® 100" by the company Calgon (and its homologues of low weight-average molecular mass) and copolymers of diallyldimethylammonium chloride and of acrylamide, sold under the name "Merquat® 550".

(10) The quaternary diammonium polymer containing repeating units corresponding to the formula:

in which formula (XI):

$R_{10}$, $R_{11}$, $R_{12}$ and $R_{13}$, which may be identical or different, represent aliphatic, alicyclic or arylaliphatic radicals containing from 1 to 20 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second hetero atom other than nitrogen, or alternatively $R_{10}$, $R_{11}$, $R_{12}$ and $R_{13}$ represent a linear or branched $C_1$–$C_6$ alkyl radical substituted with a nitrile, ester, acyl or amide group or a group —CO—O—$R_{14}$—D or —CO—NH—$R_{14}$—D where $R_{14}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid;

$A_1$, $R_{10}$ and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group —$(CH_2)_n$—CO—D—OC—$(CH_2)_n$— in which D denotes:

a) a glycol residue of formula: —O—Z—O—, where Z denotes a linear or branched hydrocarbon-based radical or a group corresponding to one of the following formulae:

—$(CH_2$—$CH_2$—O$)_x$—$CH_2$—$CH_2$—

—[$CH_2$—$CH(CH_3)$—O]$_y$—$CH_2$—$CH(CH_3)$— where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon-based radical, or alternatively the divalent radical

—$CH_2$—$CH_2$—S—S—$CH_2$—$CH_2$—;

d) a ureylene group of formula: —NH—CO—NH—.

Preferably, X⁻ is an anion such as chloride or bromide.

These polymers generally have a number-average molecular mass of between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to formula (XII) below:

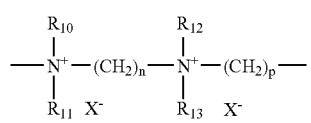

(XII)

in which $R_{10}$, $R_{11}$, $R_{12}$ and $R_{13}$, which may be identical or different, denote an alkyl or hydroxyalkyl radical containing from 1 to 4 carbon atoms approximately, n and p are integers ranging from 2 to 20 approximately, and X⁻ is an anion derived from a mineral or organic acid.

(11) Polyquaternary ammonium polymers consisting of repeating units of formula (XIII):

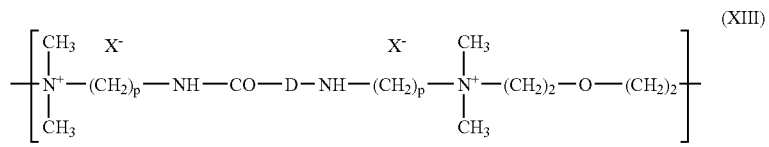

(XIII)

in which p denotes an integer ranging from 1 to 6 approximately, D may be nothing or may represent a group —$(CH_2)_r$—CO— in which r denotes a number equal to 4 or to 7, X⁻ is an anion.

Such polymers may be prepared according to the processes described in U.S. Pat. Nos. 4,157,388, 4,702,906 and 4,719,282. They are described in particular in patent application EP 122 324. Among these products, mention may be made, for example, of "Mirapol® A 15", "Mirapol® AD1", "Mirapol® AZ1" and "Mirapol® 175" sold by the company Miranol.

(12) Quaternary polymers of vinylpyrrolidone and of vinylimidazole, such as, for example, the products sold under the names Luviquat® FC 905, FC 550 and FC 370 by the company BASF.

(13) Polyamines such as Polyquart® H sold by Henkel, which is given under the reference name "Polyethylene-Glycol (15) Tallow Polyamine" in the CTFA dictionary.

(14) Crosslinked methacryloyloxy($C_1$–$C_4$)alkyltri($C_1$–$C_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, in particular methylenebisacrylamide. A crosslinked acrylamide/methacryloyloxyethyltrimethylammonium chloride copolymer (20/80 by weight) in the form of a dispersion containing 50% by weight of the said copolymer in mineral oil can be used more particularly. This dispersion is sold under the name "Salcare® SC 92" by the company Allied Colloids. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Allied Colloids.

Other cationic polymers that may be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers that may be used in the context of the present invention, it is preferred to use the polymers of families (1), (9), (10), (11), (12) and (14) and even more preferably the polymers consisting of repeating units of formulae (W) and (U) below:

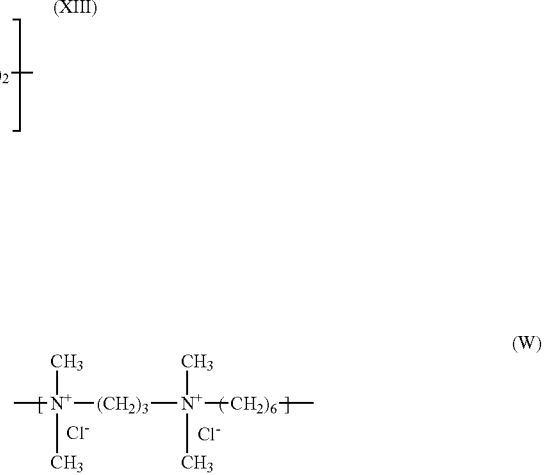

(W)

and in particular those whose molecular weight, determined by gel permeation chromatography, is between 9500 and 9900;

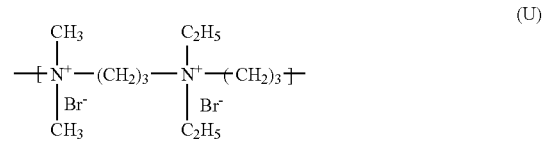

(U)

and in particular those whose molecular weight, determined by gel permeation chromatography, is about 1200.

The concentration of cationic polymer in the composition according to the present invention may range from 0.01% to 10% by weight relative to the total weight of the composition, preferably from 0.05% to 5% and even more preferably from 0.1% to 3%.

Amphoteric Polymers

The amphoteric polymers that may be used in accordance with the present invention may be chosen from polymers comprising units K and M randomly distributed in the polymer chain, in which K denotes a unit derived from a monomer comprising at least one basic nitrogen atom and M denotes a unit derived from an acidic monomer comprising one or more carboxylic or sulfonic groups, or alternatively K and M may denote groups derived from zwitterionic carboxybetaine or sulfobetaine monomers;

K and M may also denote a cationic polymer chain comprising primary, secondary, tertiary or quaternary amine groups, in which at least one of the amine groups bears a carboxylic or sulfonic group linked via a hydrocarbon-based radical, or alternatively K and M form part of a chain of a polymer containing an α,β-dicarboxylic ethylene unit in which one of the carboxylic groups has been made to react with a polyamine comprising one or more primary or secondary amine groups.

The amphoteric polymers corresponding to the above definition that are more particularly preferred are chosen from the following polymers:

(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylate and acrylate, dialkylaminoalkylmethacrylamide and -acrylamide. Such compounds are described in U.S. Pat. No. 3,836,537. Mention may also be made of the sodium acrylate/acrylamidopropyltrimethylammonium chloride copolymer sold under the name Polyquart® KE 3033 by the company Henkel.

The vinyl compound may also be a dialkyldiallylammonium salt such as dimethyldiallylammonium chloride. The copolymers of acrylic acid and of the latter monomer are sold under the names Merquat® 280, Merquat® 295 and Merquat® Plus 3330 by the company Calgon.

(2) polymers containing units derived from:
a) at least one monomer chosen from acrylamides and methacrylamides substituted on the nitrogen with an alkyl radical,
b) at least one acidic comonomer containing one or more reactive carboxylic groups, and
c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides that are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer such as the products sold under the name Amphomer® or Lovocryl® 47 by the company National Starch are particularly used.

(3) crosslinked and alkylated polyamino amides partially or totally derived from polyamino amides of general formula:

in which $R_{19}$ represents a divalent radical derived from a saturated dicarboxylic acid, a mono- or dicarboxylic aliphatic acid containing an ethylenic double bond, an ester of a lower alkanol, having 1 to 6 carbon atoms, of these acids or a radical derived from the addition of any one of the said acids to a bis(primary) or bis(secondary) amine, and Z denotes a bis(primary), mono- or bis(secondary) polyalkylenepolyamine radical and preferably represents:

a) in proportions of from 60 to 100 mol %, the radical

where x=2 and p=2 or 3, or alternatively x=3 and p=2 this radical being derived from diethylenetriamine, from triethylenetetraamine or from dipropylenetriamine;

b) in proportions of from 0 to 40 mol %, the radical (XV) above in which x=2 and p=1 and which is derived from ethylenediamine, or the radical derived from piperazine:

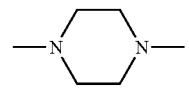

c) in proportions of from 0 to 20 mol %, the —NH—$(CH_2)_6$—NH— radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid and acids containing an ethylenic double bond such as, for example, acrylic acid, methacrylic acid and itaconic acid.

The alkane sultones used in the alkylation are preferably propane sultone or butane sultone, and the salts of the alkylating agents are preferably the sodium or potassium salts.

(4) polymers containing zwitterionic units of formula:

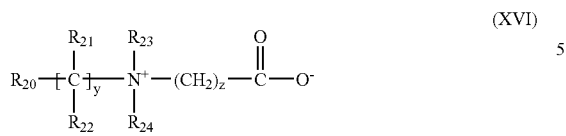

(XVI)

in which $R_{20}$ denotes a polymerizable unsaturated group such as an acrylate, methacrylate, acrylamide or methacrylamide group, y and z represent an integer from 1 to 3, $R_{21}$ and $R_{22}$ represent a hydrogen atom, methyl, ethyl or propyl, $R_{23}$ and $R_{24}$ represent a hydrogen atom or an alkyl radical such that the sum of the carbon atoms in $R_{23}$ and $R_{24}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of methyl methacrylate/dimethylcarboxymethylammonioethyl methyl methacrylate such as the product sold under the name Diaformer® Z301 by the company Sandoz.

(5) polymers derived from chitosan, containing monomer units corresponding to formulae (XVII), (XVIII) and (XIX) below:

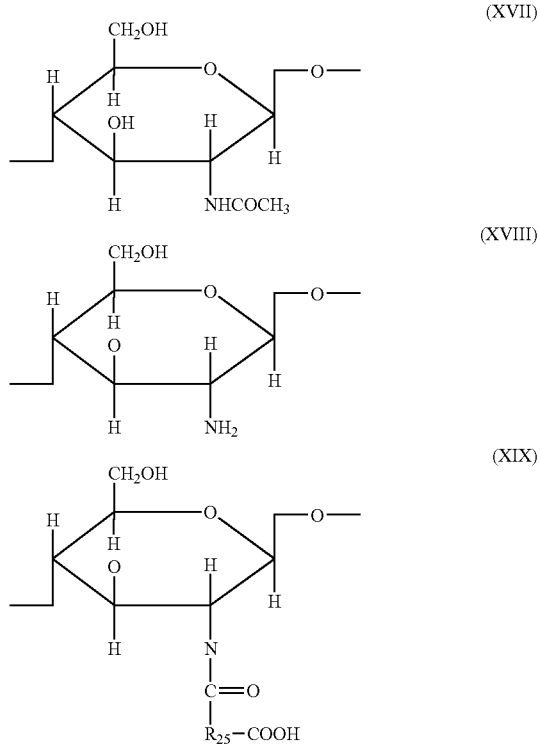

the unit (XVII) being present in proportions of between 0 and 30%, the unit (XVIII) in proportions of between 5% and 50% and the unit (XIX) in proportions of between 30% and 90%, it being understood that, in this unit (XIX), $R_{25}$ represents a radical of formula:

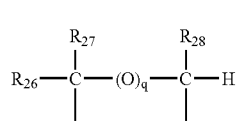

in which q denotes zero or 1;

if q=0, $R_{26}$, $R_{27}$ and $R_{28}$, which may be identical or different, each represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulfonic groups, an alkylthio residue in which the alkyl group bears an amino residue, at least one of the radicals $R_{26}$, $R_{27}$ and $R_{28}$ being, in this case, a hydrogen atom;

or, if q=1, $R_{26}$, $R_{27}$ and $R_{28}$ each represent a hydrogen atom, and also the salts formed by these compounds with bases or acids.

(6) polymers derived from the N-carboxyalkylation of chitosan, such as N-carboxymethylchitosan or N-carboxybutylchitosan sold under the name "Evalsan®" by the company Jan Dekker.

(7) polymers corresponding to the general formula (XX) as described, for example, in French patent 1 400 366:

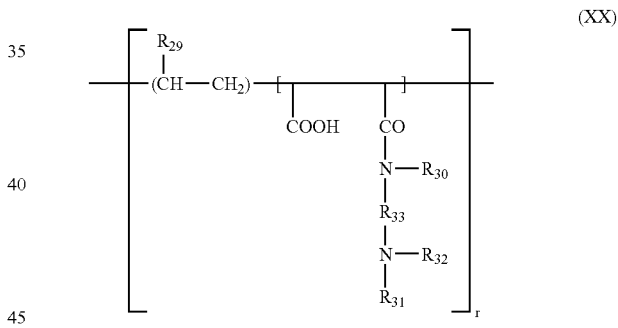

in which $R_{29}$ represents a hydrogen atom, a $CH_3O$, $CH_3CH_2O$ or phenyl radical, $R_{30}$ denotes hydrogen or a lower alkyl radical such as methyl or ethyl, $R_{31}$ denotes hydrogen or a lower alkyl radical such as methyl or ethyl, $R_{32}$ denotes a lower alkyl radical such as methyl or ethyl or a radical corresponding to the formula: $-R_{33}-N(R_{31})_2$, $R_{33}$ representing a $-CH_2-CH_2-$, $-CH_2-CH_2-CH_2-$ or $-CH_2-CH(CH_3)-$ group, $R_{31}$ having the meanings mentioned above, and also the higher homologues of these radicals and containing up to 6 carbon atoms, r is such that the molecular weight is between 500 and 6 000 000 and preferably between 1000 and 1 000 000.

(8) amphoteric polymers of the type $-D-X-D-X-$ chosen from:

a) polymers obtained by the action of chloroacetic acid or sodium chloroacetate on compounds containing at least one unit of formula:

$-D-X-D-X-D-$ (XXI)

where D denotes a radical

and X denotes the symbol E or E', E or E', which may be identical or different, denote a divalent radical which is an alkylene radical with a straight or branched chain containing up to 7 carbon atoms in the main chain, which is unsubstituted or substituted with hydroxyl groups and which can contain, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula:

$$-D-X-D-X-$$ (XXII)

where D denotes a radical

and X denotes the symbol E or E' and at least once E'; E having the meaning given above and E' being a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) $(C_1-C_5)$alkyl vinyl ether/maleic anhydride copolymers partially modified by semi-amidation with an N,N-dialkylaminoalkylamine such as N,N-dimethylaminopropylamine or by semi-esterification with an N,N-dialkanolamine. These copolymers can also contain other vinyl comonomers such as vinylcaprolactam.

The amphoteric polymers that are particularly preferred according to the invention are those of family (1).

Associative Polymers that may be Used According to the Invention

Associative polymers are water-soluble polymers capable, in an aqueous medium, of reversibly associating with each other or with other molecules.

Their chemical structure comprises hydrophilic zones and hydrophobic zones characterized by at least one fatty chain.

The associative polymers according to the invention may be of anionic, cationic or amphoteric type and are preferably nonionic or cationic.

Associative Polymers of Anionic Type:

Among these, mention may be made of:

(I) those comprising at least one hydrophilic unit and at least one fatty-chain allyl ether unit, more particularly those in which the hydrophilic unit consists of an ethylenic unsaturated anionic monomer, even more particularly of a vinylcarboxylic acid and most particularly of an acrylic acid, a methacrylic acid or mixtures thereof, the fatty-chain allyl ether unit thereof corresponding to the monomer of formula (I) below:

$$CH_2=C(R')CH_2OB_nR \qquad (I)$$

in which R' denotes H or $CH_3$, B denotes an ethyleneoxy radical, n is zero or denotes an integer ranging from 1 to 100, R denotes a hydrocarbon-based radical chosen from alkyl, arylalkyl, aryl, alkylaryl and cycloalkyl radicals, containing from 8 to 30 carbon atoms, preferably 10 to 24 carbon atoms and even more particularly from 12 to 18 carbon atoms. A unit of formula (I) that is more particularly preferred is a unit in which R' denotes H, n is equal to 10 and R denotes a stearyl ($C_{18}$) radical.

Anionic associative polymers of this type are described and prepared, according to an emulsion polymerization process, in patent EP-0 216 479.

Among these anionic associative thickening polymers that are particularly preferred according to the invention are polymers formed from 20% to 60% by weight of acrylic acid and/or of methacrylic acid, from 5% to 60% by weight of lower alkyl(meth)acrylates, from 2% to 50% by weight of fatty-chain allyl ether of formula (I), and from 0% to 1% by weight of a crosslinking agent that is a well-known copolymerizable unsaturated polyethylenic monomer, for instance diallyl phthalate, allyl(meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl ether (Steareth-10), in particular those sold by the company Allied Colloids under the names Salcare SC 80® and Salcare SC 90®, which are aqueous 30% emulsions of a crosslinked terpolymer of methacrylic acid, of ethyl acrylate and of steareth-10 allyl ether (40/50/10).

(II) those comprising at least one hydrophilic unit of olefinic unsaturated carboxylic acid type, and at least one hydrophobic unit of unsaturated carboxylic acid ($C_{10}-C_{30}$) alkyl ester type.

Preferably, these polymers are chosen from those in which the hydrophilic unit of unsaturated olefinic carboxylic acid type corresponds to the monomer of formula (II) below:

in which $R_1$ denotes H, $CH_3$ or $C_2H_5$, i.e. acrylic acid, methacrylic acid or ethacrylic acid units, and in which the hydrophobic unit of the type such as a ($C_{10}-C_{30}$) alkyl ester of an unsaturated carboxylic acid corresponds to the monomer of formula (III) below:

in which formula $R_2$ denotes H or $CH_3$ or $C_2H_5$ (i.e. acrylate, methacrylate or ethacrylate units) and preferably H (acrylate units) or $CH_3$ (methacrylate units), $R_3$ denoting a $C_{10}$–$C_{30}$ and preferably $C_{12}$–$C_{22}$ alkyl radical.

($C_{10}$–$C_{30}$)Alkyl esters of unsaturated carboxylic acids in accordance with the invention comprise, for example, lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate and dodecyl methacrylate.

Anionic polymers of this type are disclosed and prepared, for example, according to U.S. Pat. Nos. 3,915,921 and 4,509,949.

Among the associative anionic polymers of this type that will be used more particularly are polymers formed from a mixture of monomers comprising:
(i) essentially acrylic acid,
(ii) an ester of formula (III) described above, in which $R_2$ denotes H or $CH_3$, $R_3$ denoting an alkyl radical containing from 12 to 22 carbon atoms,
(iii) a crosslinking agent, which is a well-known copolymerizable polyethylenic unsaturated monomer, for instance diallyl phthalate, allyl (meth)acrylate, divinylbenzene, (poly)ethylene glycol dimethacrylate or methylenebisacrylamide.

Among the associative anionic polymers of this type that will be used more particularly are those consisting of from 95% to 60% by weight of acrylic acid (hydrophilic unit), 4% to 40% by weight of $C_{10}$–$C_{30}$ alkyl acrylate (hydrophobic unit) and 0% to 6% by weight of crosslinking polymerizable monomer, or alternatively those consisting of from 98% to 96% by weight of acrylic acid (hydrophilic unit), 1% to 4% by weight of $C_{10}$–$C_{30}$ alkyl acrylate (hydrophobic unit) and 0.1% to 0.6% by weight of crosslinking polymerizable monomer such as those described above.

Among the said above polymers, those most particularly preferred according to the present invention are the products sold by the company Goodrich under the trade names Pemulen TR1®, Pemulen TR2® and Carbopol 1382®, and even more preferentially Pemulen TR1 ®, and the product sold by the company SEPPIC under the name Coatex SX.
(III) maleic anhydride/$C_{30}$–$C_{38}$ α-olefin/alkyl maleate terpolymers, such as the product (maleic anhydride/$C_{30}$–$C_{38}$ α-olefin/isopropyl maleate copolymer) sold under the name Performa V 1608' by the company Newphase Technologies.
(IV) acrylic terpolymers comprising:
(a) about 20% to 70% by weight of a carboxylic acid containing α,β-monoethylenic unsaturation,
(b) about 20% to 80% by weight of a non-surfactant monomer containing α,β-monoethylenic unsaturation other than (a),
(c) about 0.5% to 60% by weight of a nonionic monourethane that is the product of reaction of a monohydric surfactant with a monoisocyanate containing monoethylenic unsaturation, such as those described in patent application EP-A-0 173 109 and more particularly the terpolymer described in Example 3, namely a methacrylic acid/methyl acrylate/behenyl alcohol dimethyl-meta-isopropenylbenzylisocyanate ethoxylated (40 EO) terpolymer, as an aqueous 25% dispersion.
(V) copolymers comprising among their monomers a carboxylic acid containing α,β-monoethylenic unsaturation and of an ester of a carboxylic acid containing α,β-monoethylenic unsaturation and of an oxyalkylenated fatty alcohol.

Preferentially, these compounds also comprise as monomer an ester of a carboxylic acid containing α,β-monoethylenic unsaturation and of a $C_1$–$C_4$ alcohol.

An example of a compound of this type that may be mentioned is Aculyn 22® sold by the company Rohm & Haas, which is a methacrylic acid/ethyl acrylate/stearyl methacrylate oxyalkylenated terpolymer.

Associative Polymers of Cationic Type

Among these, mention may be made of:
(I) cationic associative polyurethanes, the family of which has been described by the Applicant in French patent application No. 00/09609; it may be represented by the general formula (Ia) below:

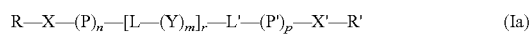

$$R-X-(P)_n-[L-(Y)_m]_r-L'-(P')_p-X'-R' \quad (Ia)$$

in which:
R and R', which may be identical or different, represent a hydrophobic group or a hydrogen atom;
X and X', which may be identical or different, represent a group comprising an amine function optionally bearing a hydrophobic group, or alternatively a group L";
L, L' and L", which may be identical or different, represent a group derived from a diisocyanate;
P and P', which may be identical or different, represent a group comprising an amine function optionally bearing a hydrophobic group;
Y represents a hydrophilic group;
r is an integer between 1 and 100, preferably between 1 and 50 and in particular between 1 and 25;
n, m and p each range, independently of each other, from 0 to 1000;
the molecule containing at least one protonated or quaternized amine function and at least one hydrophobic group.

In one preferred embodiment of these polyurethanes, the only hydrophobic groups are the groups R and R' at the chain ends.

One preferred family of cationic associative polyurethanes is the one corresponding to formula (Ia) described above and in which:
R and R' both independently represent a hydrophobic group,
X and X' each represent a group L",
n and p are between 1 and 1000, and
L, L', L", P, P', Y and m have the meaning given above.

Another preferred family of cationic associative polyurethanes is the one corresponding to formula (Ia) above in which:
R and R' both independently represent a hydrophobic group, X and X' each represent a group L", n and p are 0, and L, L', L", Y and m have the meaning given above.

The fact that n and p are 0 means that these polymers do not comprise units derived from a monomer containing an amine function, incorporated into the polymer during the polycondensation. The protonated amine functions of these polyurethanes result from the hydrolysis of excess isocyanate functions, at the chain end, followed by alkylation of the primary amine functions formed with alkylating agents containing a hydrophobic group, i.e. compounds of the type RQ or R'Q, in which R and R' are as defined above and Q denotes a leaving group such as a halide, a sulfate, etc.

Yet another preferred family of cationic associative polyurethanes is the one corresponding to formula (Ia) above in which:
R and R' both independently represent a hydrophobic group,
X and X' both independently represent a group comprising a quaternary amine, n and p are zero, and L, L', Y and m have the meaning given above.

The number-average molecular mass of the cationic associative polyurethanes is preferably between 400 and 500 000, in particular between 1000 and 400 000 and ideally between 1000 and 300 000.

The expression "hydrophobic group" means a radical or polymer containing a saturated or unsaturated, linear or branched hydrocarbon-based chain, which may contain one or more hetero atoms such as P, O, N or S, or a radical containing a perfluoro or silicone chain. When the hydrophobic group denotes a hydrocarbon-based radical, it comprises at least 10 carbon atoms, preferably from 10 to 30 carbon atoms, in particular from 12 to 30 carbon atoms and more preferably from 18 to 30 carbon atoms.

Preferentially, the hydrocarbon-based group is derived from a monofunctional compound.

By way of example, the hydrophobic group may be derived from a fatty alcohol such as stearyl alcohol, dodecyl alcohol or decyl alcohol. It may also denote a hydrocarbon-based polymer such as, for example, polybutadiene.

When X and/or X' denote(s) a group comprising a tertiary or quaternary amine, X and/or X' may represent one of the following formulae:

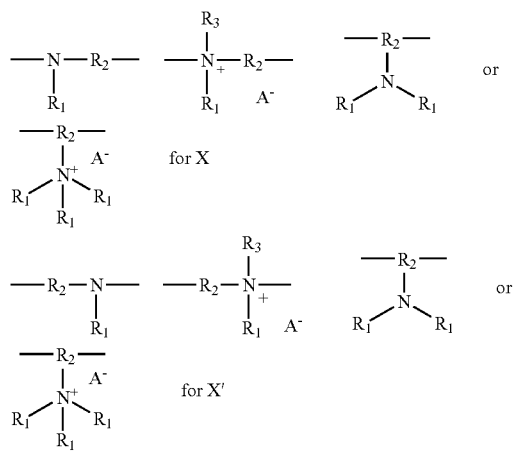

in which:
R$_2$ represents a linear or branched alkylene radical containing from 1 to 20 carbon atoms, optionally comprising a saturated or unsaturated ring, or an arylene radical, one or more of the carbon atoms possibly being replaced with a hetero atom chosen from N, S, O and P;

R$_1$ and R$_3$, which may be identical or different, denote a linear or branched C$_1$–C$_{30}$ alkyl or alkenyl radical or an aryl radical, at least one of the carbon atoms possibly being replaced with a hetero atom chosen from N, S, O and P;

A$^-$ is a physiologically acceptable counterion.

The groups L, L' and L" represent a group of formula:

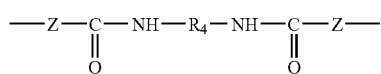

in which:
Z represents —O—, —S— or —NH—; and

R$_4$ represents a linear or branched alkylene radical containing from 1 to 20 carbon atoms, optionally comprising a saturated or unsaturated ring, or an arylene radical, one or more of the carbon atoms possibly being replaced with a hetero atom chosen from N, S, O and P.

The groups P and P' comprising an amine function may represent at least one of the following formulae:

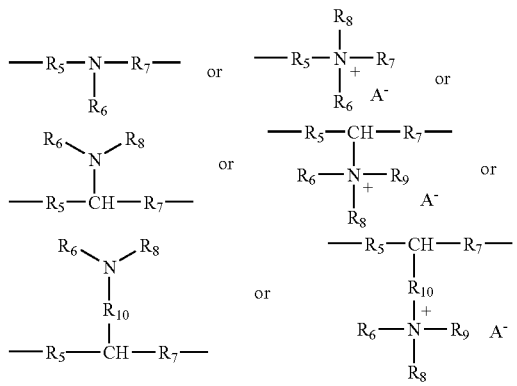

in which:
R$_5$ and R$_7$ have the same meanings as R$_2$ defined above;

R$_6$, R$_8$ and R$_9$ have the same meanings as R$_1$ and R$_3$ defined above;

R$_{10}$ represents a linear or branched, optionally unsaturated alkylene group possibly containing one or more hetero atoms chosen from N, O, S and P; and A$^-$ is a physiologically acceptable counterion.

As regards the meaning of Y, the term "hydrophilic group" means a polymeric or non-polymeric water-soluble group.

By way of example, when it is not a polymer, mention may be made of ethylene glycol, diethylene glycol and propylene glycol.

When it is a hydrophilic polymer, in accordance with one preferred embodiment, mention may be made, for example, of polyethers, sulfonated polyesters, sulfonated polyamides or a mixture of these polymers. The hydrophilic compound is preferentially a polyether and in particular a poly(ethylene oxide) or poly(propylene oxide).

The cationic associative polyurethanes of formula (Ia) according to the invention are formed from diisocyanates and from various compounds with functions containing a labile hydrogen. The functions containing a labile hydrogen may be alcohol, primary or secondary amine or thiol functions, giving, after reaction with the diisocyanate functions, polyurethanes, polyureas and polythioureas, respectively. The expression "polyurethanes" according to the present invention encompasses these three types of polymers, namely polyurethanes per se, polyureas and polythioureas, and also copolymers thereof.

A first type of compound involved in the preparation of the polyurethane of formula (Ia) is a compound comprising at least one unit containing an amine function. This compound may be multifunctional, but the compound is preferentially difunctional, that is to say that, according to one preferential embodiment, this compound comprises two labile hydrogen atoms borne, for example, by a hydroxyl, primary amine, secondary amine or thiol function. A mixture of multifunctional and difunctional compounds in which the percentage of multifunctional compounds is low may also be used.

As mentioned above, this compound may comprise more than one unit containing an amine function. In this case, it is a polymer bearing a repetition of the unit containing an amine function.

Compounds of this type may be represented by one of the following formulae:

HZ—(P)$_n$—ZH or

HZ—(P')$_p$—ZH in which Z, P, P', n and p are as defined above.

Examples of compounds containing an amine function that may be mentioned include N-methyldiethanolamine, N-tert-butyldiethanolamine and N-sulfoethyldiethanolamine.

The second compound involved in the preparation of the polyurethane of formula (Ia) is a diisocyanate corresponding to the formula:

O=C=N—R$_4$—N=C=O in which R$_4$ is defined above.

By way of example, mention may be made of methylenediphenyl diisocyanate, methylenecyclohexane diisocyanate, isophorone diisocyanate, toluene diisocyanate, naphthalene diisocyanate, butane diisocyanate and hexane diisocyanate.

A third compound involved in the preparation of the polyurethane of formula (Ia) is a hydrophobic compound intended to form the terminal hydrophobic groups of the polymer of formula (Ia).

This compound consists of a hydrophobic group and of a function containing a labile hydrogen, for example a hydroxyl, primary or secondary amine, or thiol function.

By way of example, this compound may be a fatty alcohol such as, in particular, stearyl alcohol, dodecyl alcohol or decyl alcohol. When this compound comprises a polymeric chain, it may be, for example, α-hydroxylated hydrogenated polybutadiene.

The hydrophobic group of the polyurethane of formula (Ia) may also result from the quaternization reaction of the tertiary amine of the compound comprising at least one tertiary amine unit. Thus, the hydrophobic group is introduced via the quaternizing agent. This quaternizing agent is a compound of the type RQ or R'Q, in which R and R' are as defined above and Q denotes a leaving group such as a halide, a sulfate, etc.

The cationic associative polyurethane may also comprise a hydrophilic block. This block is provided by a fourth type of compound involved in the preparation of the polymer. This compound may be multifunctional. It is preferably difunctional. It is also possible to have a mixture in which the percentage of multifunctional compound is low.

The functions containing a labile hydrogen are alcohol, primary or secondary amine or thiol functions. This compound may be a polymer terminated at the chain ends with one of these functions containing a labile hydrogen.

By way of example, when it is not a polymer, mention may be made of ethylene glycol, diethylene glycol and propylene glycol.

When it is a hydrophilic polymer, mention may be made, for example, of polyethers, sulfonated polyesters and sulfonated polyamides, or a mixture of these polymers. The hydrophilic compound is preferentially a polyether and especially a poly(ethylene oxide) or poly(propylene oxide).

The hydrophilic group termed Y in formula (Ia) is optional. Specifically, the units containing a quaternary amine or protonated function may suffice to provide the solubility or water-dispersibility required for this type of polymer in an aqueous solution.

Although the presence of a hydrophilic group Y is optional, cationic associative polyurethanes comprising such a group are, however, preferred.

(II) quaternized cellulose derivatives and polyacrylates containing non-cyclic amine side groups.

The quaternized cellulose derivatives are, in particular:
quaternized celluloses modified with groups comprising at least one fatty chain, such as alkyl, arylalkyl or alkylaryl groups containing at least 8 carbon atoms, or mixtures thereof,
quaternized hydroxyethylcelluloses modified with groups comprising at least one fatty chain, such as alkyl, arylalkyl or alkylaryl groups containing at least 8 carbon atoms, or mixtures thereof.

The alkyl radicals borne by the above quaternized celluloses or hydroxyethylcelluloses preferably contain from 8 to 30 carbon atoms. The aryl radicals preferably denote phenyl, benzyl, naphthyl or anthryl groups.

Examples of quaternized alkylhydroxyethylcelluloses containing $C_8$–$C_{30}$ fatty chains that may be mentioned include the products Quatrisoft LM 200, Quatrisoft LM-X 529-18-A®, Quatrisoft LM-X 529-18B® ($C_{12}$ alkyl) and Quatrisoft LM-X 529-8® ($C_{18}$ alkyl) sold by the company Amerchol, and the products Crodacel QM®, Crodacel QL® ($C_{12}$ alkyl) and Crodacel QS® ($C_{18}$ alkyl) sold by the company Croda.

(III) Cationic polyvinyllactams, the family of which was described by the Applicant in French patent application No. 01/01106.

The said polymers comprise:
a) at least one monomer of vinyllactam or alkylvinyllactam type;
b) at least one monomer of structure (I) or (II) below:

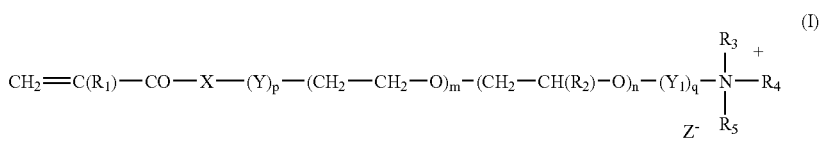

(I)

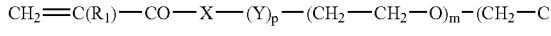   

(II)

$$CH_2=C(R_1)-CO-X-(Y)_p-(CH_2-CH_2-O)_m-(CH_2-CH(R_2)-O)_n-(Y_1)_q-N\begin{matrix}R_3\\R_4\end{matrix}$$

in which:

X denotes an oxygen atom or a radical $NR_6$, $R_1$ and $R_6$ denote, independently of each other, a hydrogen atom or a linear or branched $C_1$–$C_5$ alkyl radical, $R_2$ denotes a linear or branched $C_1$–$C_4$ alkyl radical, $R_3$, $R_4$ and $R_5$ denote, independently of each other, a hydrogen atom, a linear or branched $C_1$–$C_{30}$ alkyl radical or a radical of formula (III):

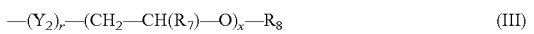

$$-(Y_2)_r-(CH_2-CH(R_7)-O)_x-R_8 \quad (III)$$

Y, $Y_1$ and $Y_2$ denote, independently of each other, a linear or branched $C_2$–$C_{16}$ alkylene radical, $R_7$ denotes a hydrogen atom, a linear or branched C1–C4 alkyl radical, or a linear or branched $C_1$–$C_4$ hydroxyalkyl radical, $R_8$ denotes a hydrogen atom or a linear or branched $C_1$–$C_{30}$ alkyl radical, p, q and r denote, independently of each other, either the value 0 or the value 1, m and n denote, independently of each other, an integer ranging from 0 to 100, x denotes an integer ranging from 1 to 100, Z denotes an organic or mineral acid anion, with the proviso that:

at least one of the substituents $R_3$, $R_4$, $R_5$ or $R_8$ denotes a linear or branched $C_9$–$C_{30}$ alkyl radical, if m or n is other than zero, then q is equal to 1, if m or n is equal to zero, then p or q is equal to 0.

The cationic poly(vinyllactam) polymers according to the invention may be crosslinked or non-crosslinked and may also be block polymers.

Preferably, the counterion $Z^-$ of the monomers of formula (I) is chosen from halide ions, phosphate ions, the methosulfate ion and the tosylate ion.

Preferably, $R_3$, $R_4$ and $R_5$ denote, independently of each other, a hydrogen atom or a linear or branched $C_1$–$C_{30}$ alkyl radical.

More preferably, the monomer b) is a monomer of formula (I) for which, even more preferably, m and n are equal to zero.

The vinyllactam or alkylvinyllactam monomer is preferably a compound of structure (IV):

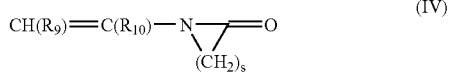

$$CH(R_9)=C(R_{10})-N\underset{(CH_2)_s}{\diagdown\!\!\!\diagup}=O \quad (IV)$$

in which:

s denotes an integer ranging from 3 to 6, $R_9$ denotes a hydrogen atom or a $C_1$–$C_5$ alkyl radical, $R_{10}$ denotes a hydrogen atom or a $C_1$–$C_5$ alkyl radical, with the proviso that at least one of the radicals $R_9$ and $R_{10}$ denotes a hydrogen atom.

Even more preferably, the monomer (IV) is vinylpyrrolidone.

The cationic poly(vinyllactam) polymers according to the invention may also contain one or more additional monomers, preferably cationic or nonionic monomers.

As compounds that are more particularly preferred according to the invention, mention may be made of the following terpolymers comprising at least:

a) one monomer of formula (IV), b) one monomer of formula (I) in which p=1, q=0, $R_3$ and $R_4$ denote, independently of each other, a hydrogen atom or a $C_1$–$C_5$ alkyl radical and $R_5$ denotes a $C_9$–$C_{24}$ alkyl radical, and c) a monomer of formula (II) in which $R_3$ and $R_4$ denote, independently of each other, a hydrogen atom or a $C_1$–$C_5$ alkyl radical.

Even more preferably, terpolymers comprising, by weight, 40% to 95% of monomer (a), 0.1% to 55% of monomer (c) and 0.25% to 50% of monomer (b) will be used. Such polymers are described in patent application WO-00/68282, the content of which forms an integral part of the invention.

As cationic poly(vinyllactam) polymers according to the invention, vinylpyrrolidone/dimethylaminopropylmethacrylamide/dodecyldimethylmethacrylamidopropylammonium tosylate terpolymers, vinylpyrrolidone/dimethylaminopropylmethacrylamide/cocoyl-dimethylmethacrylamidopropylammonium tosylate terpolymers, vinylpyrrolidone/dimethylaminopropylmethacrylamide/lauryldimethylmethacrylamidopropylammonium tosylate or chloride terpolymers are used in particular.

The weight-average molecular mass of the cationic poly(vinyllactam) polymers according to the present invention is preferably between 500 and 20 000 000. It is more particularly between 200 000 and 2 000 000 and even more preferentially between 400 000 and 800 000.

Amphoteric Associative Polymers

These polymers are preferably chosen from those comprising at least one non-cyclic cationic unit. Even more particularly, the ones that are preferred are those prepared from or comprising 1 to 20 mol %, preferably 1.5 to 15 mol % and even more particularly 1.5 to 6 mol % of fatty-chain monomer relative to the total number of moles of monomers.

The amphoteric associative polymers that are preferred according to the invention comprise or are prepared by copolymerizing:

1) at least one monomer of formula (Ia) or (Ib):

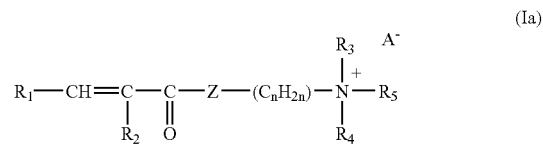

$$R_1-CH=C\underset{R_2}{\overset{}{|}}-\underset{O}{\overset{}{C}}-Z-(C_nH_{2n})-\underset{R_4}{\overset{R_3\ A^-}{\underset{|}{\overset{|+}{N}}}}-R_5 \quad (Ia)$$

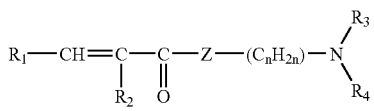

in which $R_1$ and $R_2$, which may be identical or different, represent a hydrogen atom or a methyl radical, $R_3$, $R_4$ and $R_5$, which may be identical or different, represent a linear or branched alkyl radical containing from 1 to 30 carbon atoms, Z represents an NH group or an oxygen atom, n is an integer from 2 to 5, $A^-$ is an anion derived from an organic or mineral acid, such as a methosulfate anion or a halide such as chloride or bromide;

2) at least one monomer of formula (II)

in which $R_6$ and $R_7$, which may be identical or different, represent a hydrogen atom or a methyl radical; and 3) at least one monomer of formula (III):

in which $R_6$ and $R_7$, which may be identical or different, represent a hydrogen atom or a methyl radical, X denotes an oxygen or nitrogen atom and $R_8$ denotes a linear or branched alkyl radical containing from 1 to 30 carbon atoms;

at least one of the monomers of formula (Ia), (Ib) or (III) comprising at least one fatty chain.

The monomers of formulae (Ia) and (Ib) of the present invention are preferably chosen from the group consisting of:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, dimethylaminopropylacrylamide, these monomers optionally being quaternized, for example with a $C_1$–$C_4$ alkyl halide or a $C_1$–$C_4$ dialkyl sulfate.

More particularly, the monomer of formula (Ia) is chosen from acrylamidopropyltrimethylammonium chloride and methacrylamidopropyltrimethylammonium chloride.

The monomers of formula (II) of the present invention are preferably chosen from the group consisting of acrylic acid, methacrylic acid, crotonic acid and 2-methylcrotonic acid. More particularly, the monomer of formula (II) is acrylic acid.

The monomers of formula (III) of the present invention are preferably chosen from the group consisting of $C_{12}$–$C_{22}$ and more particularly $C_{16}$–$C_{18}$ alkyl acrylates or methacrylates.

The monomers constituting the fatty-chain amphoteric polymers of the invention are preferably already neutralized and/or quaternized.

The ratio of the number of cationic charges/anionic charges is preferably equal to about 1.

The amphoteric associative polymers according to the invention preferably comprise from 1 mol % to 10 mol % of the monomer comprising a fatty chain (monomer of formula (Ia), (Ib) or (III)), and preferably from 1.5 mol % to 6 mol %.

The weight-average molecular weights of the amphoteric associative polymers according to the invention may range from 500 to 50 000 000 and are preferably between 10 000 and 5 000 000.

The amphoteric associative polymers according to the invention may also contain other monomers such as non-ionic monomers and in particular such as $C_1$–$C_4$ alkyl acrylates or methacrylates.

Amphoteric associative polymers according to the invention are described and prepared, for example, in patent application WO 98/44012.

Among the amphoteric associative polymers according to the invention, the ones that are preferred are acrylic acid/(meth)acrylamidopropyltrimethylammonium chloride/stearyl methacrylate terpolymers.

Associative Polymers of Nonionic Type

According to the invention, they are preferably chosen from:

(1) celluloses modified with groups comprising at least one fatty chain;

examples that may be mentioned include:

hydroxyethylcelluloses modified with groups comprising at least one fatty chain, such as alkyl, arylalkyl or alkylaryl groups, or mixtures thereof, and in which the alkyl groups are preferably $C_8$–$C_{22}$, for instance the product Natrosol Plus Grade 330 CS® ($C_{16}$ alkyls) sold by the company Aqualon, or the product Bermocoll EHM 100® sold by the company Berol Nobel, those modified with alkylphenyl polyalkylene glycol ether groups, such as the product Amercell Polymer HM-1500® (nonylphenyl polyethylene glycol (15) ether) sold by the company Amerchol.

(2) hydroxypropyl guars modified with groups comprising at least one fatty chain, such as the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhodia.

(3) copolymers of vinylpyrrolidone and of fatty-chain hydrophobic monomers; examples thereof that may be mentioned include:

the products Antaron V216® or Ganex V216® (vinylpyrrolidone/hexadecene copolymer) sold by the company ISP the products Antaron V220' or Ganex V220® (vinylpyrrolidone/eicosene copolymer) sold by the company ISP (4) copolymers of $C_1$–$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208®.

(5) copolymers of hydrophilic methacrylates or acrylates and of hydrophobic monomers comprising at least one fatty chain, such as, for example, the polyethylene glycol methacrylate/lauryl methacrylate copolymer.

(6) polyurethane polyethers comprising in their chain both hydrophilic blocks usually of polyoxyethylenated nature and hydrophobic blocks, which may be aliphatic sequences alone and/or cycloaliphatic and/or aromatic sequences.

(7) polymers with an aminoplast ether skeleton containing at least one fatty chain, such as the Pure Thix® compounds sold by the company Sud-Chemie.

Preferably, the polyurethane polyethers comprise at least two hydrocarbon-based lipophilic chains containing from 6 to 30 carbon atoms, separated by a hydrophilic block, the hydrocarbon-based chains possibly being pendent chains, or chains at the end of the hydrophilic block. In particular, it is possible for one or more pendent chains to be included. In addition, the polymer may comprise a hydrocarbon-based chain at one end or at both ends of a hydrophilic block.

The polyurethane polyethers may be multiblock, in particular in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

The nonionic fatty-chain polyurethane polyethers may be triblock copolymers in which the hydrophilic block is a polyoxyethylenated chain comprising from 50 to 1 000 oxyethylene groups. The nonionic polyurethane polyethers comprise a urethane linkage between the hydrophilic blocks, whence arises the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, it is also possible to use Rheolate 205® containing a urea function, sold by the company Rheox, or Rheolate® 208, 204 or 212, and also Acrysol RM 184®.

Mention may also be made of the product Elfacos T210® containing a $C_{12-14}$ alkyl chain, and the product Elfacos T212® containing a $C_{18}$ alkyl chain, from Akzo.

The product DW 1206B® from Rohm & Haas containing a $C_{20}$ alkyl chain and a urethane linkage, sold at a solids content of 20% in water, may also be used.

It is also possible to use solutions or dispersions of these polymers, especially in water or in aqueous-alcoholic medium. Examples of such polymers that may be mentioned are Rheolate® 255, Rheolate® 278 and Rheolate® 244 sold by the company Rheox. The products DW 1206F and DW 1206J sold by the company Rohm & Haas may also be used.

The polyurethane polyethers that may be used according to the invention are in particular those described in the article by G. Fonnum, J. Bakke and Fk. Hansen—Colloid Polym. Sci 271, 380.389 (1993).

Even more particularly, according to the invention, it is preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold especially by the company Rohm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexyl-isocyanate) (SMDI), at 35% by weight in a mixture of propylene glycol (39%) and water (26%)].

The cationic polymers and the amphoteric polymers may represent approximately from 0.01% to 10% by weight, preferably from 0.05% to 5% by weight and even more preferentially from 0.1% to 3% by weight of the total weight of the composition.

The associative polymers may represent approximately from 0.01% to 10% of the total weight of the composition and preferably from 0.1% to 5% by weight relative to the total weight of the composition.

Medium

The medium for the dye composition that is suitable for dyeing is preferably an aqueous medium consisting of water and can advantageously contain one or more cosmetically acceptable organic solvents and more particularly linear or branched, preferably saturated, monoalcohols or diols, containing from 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol, or glycols or glycol ethers such as, for example, ethylene glycol monomethyl, monoethyl or monobutyl ether, propylene glycol or its ethers such as, for example, propylene glycol monomethyl ether, butylene glycol or dipropylene glycol, and also diethylene glycol $(C_1-C_4)$alkyl ethers such as, for example, diethylene glycol monoethyl ether or monobutyl ether, alone or as mixtures.

The solvents may then each be present in concentrations of between 0.5% and 20% by weight relative to the total weight of the composition. More particularly, the solvent content is at least 2% by weight and preferably at least 5% by weight relative to the total weight of the composition. Moreover, it is preferably less than or equal to 20% by weight and advantageously less than or equal to 15% by weight relative to the total weight of the composition.

Other Adjuvants

The dye composition according to the invention may also comprise an effective amount of other agents, known previously elsewhere in oxidation dyeing, such as various common adjuvants, for instance sequestering agents such as EDTA and etidronic acid, UV screening agents, screening agents, waxes, volatile or non-volatile, cyclic or linear or branched silicones, which are optionally organomodified (in particular with amine groups), preserving agents, ceramides, pseudoceramides, vitamins or provitamins, for instance panthenol, opacifiers, etc.

According to one variant, the composition may comprise at least one fatty substance, for instance chosen among linear or branched, saturated fatty alcohols containing at least 10 carbon atoms, saturated oils or waxes, of plant origin, hydrocarboned. Advantageously if such compounds are present, their total content is of less than or equal to 10% by weight of the composition.

The said composition may also comprise reducing agents or antioxidants. These agents may be chosen in particular from sodium sulfite, thioglycolic acid, thiolactic acid, sodium bisulfite, dehydroascorbic acid, hydroquinone, 2-methylhydroquinone, tert-butylhydroquinone and homogentisic acid, and, in this case, they are generally present in amounts ranging from about 0.05% to 1.5% by weight relative to the total weight of the composition.

The dye composition in accordance with the invention may also comprise unsaturated fatty alcohols, for instance oleyl alcohol, in a weight proportion ranging from 0.5% to 15% relative to the total weight of the dye composition.

Needless to say, a person skilled in the art will take care to select the optional additional compound(s) mentioned above such that the advantageous properties intrinsically associated with the ready-to-use composition according to the invention are not, or are not substantially, adversely affected by the envisaged addition(s).

In accordance with one particular embodiment of the invention, the composition, before mixing with the oxidizing composition, is in the form of a liquid at 25° C. and at atmospheric pressure.

Preferably, the said liquid has a viscosity of not more than 150 cPs, measured using a RheoStress 1 rheometer, at a shear rate of 200 $s^{-1}$, at 25° C.

Oxidizing Agent

In the oxidizing composition, the oxidizing agent is preferably chosen from hydrogen peroxide, urea peroxide, alkali metal bromates or ferricyanides, and persalts such as perborates and persulfates. It is particularly preferred to use hydrogen peroxide. This oxidizing agent advantageously consists of an aqueous hydrogen peroxide solution whose titre may range, more particularly, from about 1 to 40 volumes and even more preferably from about 5 to 40 volumes.

Oxidizing agents that may also be used are one or more redox enzymes such as laccases, peroxidases and 2-electron oxidoreductases (such as uricase), where appropriate in the presence of the respective donor or cofactor thereof.

The pH of the ready-to-use composition applied to the keratin fibres [composition resulting from mixing together the dye composition and the oxidizing composition] is generally between 3 and 12, limits included. It is preferably between 8.5 and 11 limits included and may be adjusted to the desired value using acidifying or basifying agents that are well known in the prior art in the dyeing of keratin fibres.

Among the basifying agents that may be mentioned, for example, are aqueous ammonia, alkali metal carbonates, alkanolamines such as monoethanolamine, diethanolamine and triethanolamine and derivatives thereof, oxyethylenated and/or oxypropylenated hydroxyalkylamines and ethylenediamines, sodium hydroxide, potassium hydroxide and the compounds having the following formula:

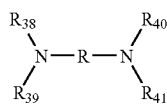

in which R is a propylene residue optionally substituted with a hydroxyl group or a $C_1$–$C_4$ alkyl radical; $R_{38}$, $R_{39}$, $R_{40}$ and $R_{41}$, which may be identical or different, represent a hydrogen atom, a $C_1$–$C_4$ alkyl radical or a $C_1$–$C_4$ hydroxyalkyl radical.

The acidifying agents are conventionally, for example, mineral or organic acids, for instance hydrochloric acid, orthophosphoric acid, carboxylic acids, for instance tartaric acid, citric acid or lactic acid, or sulfonic acids.

The dyeing process according to the invention preferably consists in applying the ready-to-use composition, prepared extemporaneously at the time of use from the dye composition and the oxidizing composition described above, to wet or dry keratin fibres, and leaving the composition to act for a leave-in time preferably ranging from 1 to 60 minutes approximately and more preferentially from 10 to 45 minutes approximately, rinsing the fibres and then optionally washing them with shampoo, and then rinsing them again and drying them.

A concrete example illustrating the invention is given below, without, however, being limiting in nature.

EXEMPLE

The dye composition below was prepared:

Dye Composition:

(expressed as grams of Active Material)

| | |
|---|---|
| Lauryl ether carboxylic acid 4.5 EO (Akypo ® RLM 45 sold by Chem Y) | 7 |
| Lauryl alcohol 2 EO (Dehydol ® LS-2-DEO-N sold by Cognis) | 4 |
| Decyl alcohol 5 EO (Empilan ® KA-5/90-FL sold by Albright & Wilson) | 8 |
| Oleyl alcohol | 3 |
| Rapeseed fatty acid amide containing 4 mol of ethylene oxide (Aminol ® N sold by Chem Y) | 7 |
| Nonionic associative polymer (Dapral ® T212 sold by Akzo) | 1 |
| Monoethanolamine | 2 |
| Polyquaternium-6 (Merquat 100 sold by Calgon) | 1.5 |
| Ethanol | 11 |
| Propylene glycol | 5 |
| Dipropylene glycol | 5 |
| 1,3-Dihydroxybenzene (resorcinol) | 0.3 |
| para-Phenylenediamine | 0.3 |
| Reducing agents, antioxidants | qs |
| Sequestering agent | qs |
| Fragrance | qs |
| Aqueous ammonia (containing 20.5% ammonia) | 1.6 |
| Demineralized water qs | 100 |

The dye composition was mixed, at the time of use, in a plastic bowl and for two minutes, with an oxidizing composition having a titre of aqueous hydrogen peroxide solution of 20 volumes, in a proportion of 1 part of dye composition per 1.5 parts of oxidizing composition.

The mixture obtained was applied to locks of hair containing 90% white hairs, and was left on for 30 minutes.

The locks were then rinsed with water, washed with shampoo, rinsed again with water and then dried and disentangled.

A greenish-brown shade was thus obtained.

EXAMPLE 2

The dye compositions below were prepared:

Dye Compositions:

(amounts expressed as grams of active material)

| | Composition A Invention | Composition B Comparative |
|---|---|---|
| Propylene glycol | 5 | 5 |
| Oxyethylenated rapeseed fatty acid amide (4 EO) | 7 | 3 |
| Lauryl ether carboxylic acid (4.5 EO) | 4.5 | 4.5 |
| Oxyethylenated decyl alcohol (3 EO) | 8.0 | 8.0 |
| Oleyl alcohol | 1 | 1 |
| Oxyethylenated lauryl alcohol (2 EO) | 4 | 4 |
| Diurethane (HMDI) of oxyethylenated (66 EO) and oxypropylenated (14 PO) alcohols (C16/C18) | 0.1 | 0.1 |
| 1,3-Dihydroxybenzene (resorcinol) | 0.3 | 0.3 |
| 1,4-Diaminobenzene | 0.3 | 0.3 |
| Pure monoethanolamine | 2 | 2 |

-continued

| | Composition A Invention | Composition B Comparative |
|---|---|---|
| Ethylenediaminetetraacetic acid | 0.2 | 0.2 |
| Erythorbic acid (or D-isoascorbic acid) | 0.31 | 0.31 |
| Dimethyldiallylammonium chloride homopolymer as an aqueous 40% solution | 1.5 | 1.5 |
| Fragrance | 0.95 | 0.95 |
| Dipropylene glycol | 5 | 5 |
| Ammonium thiolactate as an aqueous 58% solution (50% thiolactic acid) | 0.8 | 0.8 |
| Aqueous ammonia (20% reference concentration) | 8 | 8 |
| Denatured 96-degree ethyl alcohol | 11.0 | 11.0 |
| Deionized water | qs 100 | qs 100 |

The dye composition was mixed, at the time of use, with an oxidizing composition having a titre of aqueous hydrogen peroxide solution of 20 volumes, in a proportion of 1 part of dye composition per 1.5 parts of oxidizing composition.

The mixture obtained was applied in a half-head test to ten different models (one half of the head with composition A mixed with the oxidizing composition, and the other half of the head with composition B mixed with the same oxidizing composition).

The application differences between the two supports were then noted on a scale from 1 to 5, and in particular:
the adhesion at the root (1: little adhesion—5: strong adhesion)
the consistency on the head (1: quite thin—5: very thick)

On an average of ten tests, the evaluation having been performed by a panel of experts (the evaluator changing for each test), the following results were obtained:

| Adhesion | | Consistency | |
|---|---|---|---|
| A | B | A | B |
| 3.35 | 2.25 | 2.95 | 1.95 |

Composition A according to the invention, which contains 7% Aminol N, adheres to the roots much better and has much better consistency on the head (significant differences) than the comparative composition B, which contains only 3% Aminol N.

The invention claimed is:

1. A composition for the oxidation dyeing of keratin fibers, comprising, in a medium that is suitable for dyeing,
   at least one oxidation dye, and
   at least one oxyethlyenated rapeseed fatty acid amide present in an amount greater than 5% by weight relative to the total weight of the composition.

2. A composition for the oxidation dyeing wherein said keratin fibers are human hair.

3. The composition according to claim 1 wherein the at least one oxyethlyenated rapeseed fatty acid amide is chosen from those comprising 1 to 20 mol of ethylene oxide.

4. The composition according to claim 3, wherein the at least one oxyethlyenated rapeseed fatty acid amide is chosen from those comprising 1 to 10 mol of ethylene oxide.

5. The composition according to claim 4, wherein the at least one oxyethlyenated rapeseed fatty acid amide is chosen from those comprising 1 to 5 mol of ethylene oxide.

6. The composition according to claim 1, wherein the at least one oxyethlyenated rapeseed fatty acid amide is present in an amount up to 20% by weight relative to the total weight of the composition.

7. The composition according to claim 1, wherein the at least one oxyethylenated rapeseed fatty acid amide is present in the composition in an amount of at least 5.5% by weight relative to the total weight of the composition.

8. The composition according to claim 1 wherein the oxidation dye is chosen from at least one oxidation base and at least one coupler.

9. The composition according to claim 8, further comprising at least one oxidation base.

10. The composition according to claim 8, wherein the at least one oxidation base is chosen from ortho- or para-phenylenediamines, double bases, ortho- or para-aminophenols, and heterocyclic bases, and the acid-addition salts thereof.

11. The composition according to claim 10, wherein the para-phenylenediamines are chosen from the compounds of formula (I):

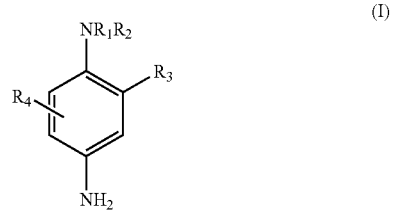

in which:
R$_1$ is chosen from a hydrogen atom, a C$_1$–C$_4$ alkyl radical, a C$_1$–C$_4$ monohydroxyalkyl radical, a C$_2$–C$_4$ polyhydroxyalkyl radical, a (C$_1$–C$_4$)alkoxy(C$_1$–C$_4$)alkyl radical and a C$_1$–C$_4$ alkyl radical substituted with a nitrogenous, phenyl or 4'-aminophenyl group;

R$_2$ is chosen from a hydrogen atom, a C$_1$–C$_4$ alkyl radical, a C$_1$–C$_4$ monohydroxyalkyl radical, a C$_2$–C$_4$ polyhydroxyalkyl radical, a (C$_1$–C$_4$)alkoxy(C$_1$–C$_4$)alkyl radical and a C$_1$–C$_4$ alkyl radical substituted with a nitrogenous group;

R$_1$ and R$_2$ may also form, with the nitrogen atom that bears them, a 5- or 6-membered nitrogenous heterocycle optionally substituted with at least one alkyl, hydroxyl or ureido group;

R$_3$ is chosen from a hydrogen atom, a halogen atom, a C$_1$–C$_4$ alkyl radical, a sulfo radical, a carboxyl radical, a C$_1$–C$_4$ monohydroxyalkyl radical, a C$_1$–C$_4$ hydroxyalkoxy radical, an acetylamino(C$_1$–C$_4$)alkoxy radical, a mesylamino(C$_1$–C$_4$)alkoxy radical and a carbamoylamino(C$_1$–C$_4$)alkoxy radical, R$_4$ is chosen from a hydrogen atom, a halogen atom and a C$_1$–C$_4$ alkyl radical.

12. The composition according to claim 11, wherein the nitrogenous groups are chosen from amino, mono(C$_1$–C$_4$) alkylamino, di(C$_1$–C$_4$)alkylamino, tri(C$_1$–C$_4$)alkylamino, monohydroxy(C$_1$–C$_4$)alkylamino, imidazolinium and ammonium radicals.

13. The composition according to claim 10 wherein the double bases are chosen from the compounds of formula (II):

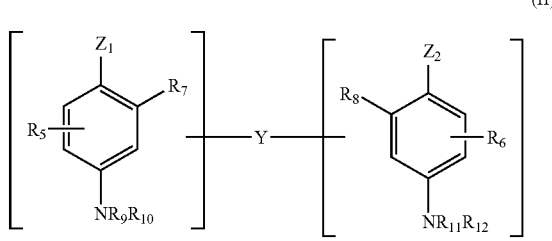

in which:

$Z_1$, and $Z_2$, which may be identical or different are chosen from hydroxyl radicals and —$NH_2$ radical which may be substituted with a $C_1$–$C_4$ alkyl radical or with a linker arm Y;

the linker arm Y is a linear or branched alkylene chain comprising from 1 to 14 carbon atoms, which may be interrupted by or terminated with at least one nitrogenous group and/or at least one hetero atom and optionally substituted with at least one hydroxyl or $C_1$–$C_6$ alkoxy radical;

$R_5$ and $R_6$ are chosen from a hydrogen atom, a halogen atom, a $C_{1-4}$ alkyl radical, a $C_1$–$C_4$ monohydroxyalkyl radical, a $C_2$–$C_4$ polyhydroxyalkyl radical, a $C_1$–$C_4$ aminoalkyl radical and a linker arm Y;

$R_7$, $R_8$, $R_9$, $R_{10}$, $R_{11}$, and $R_{12}$, which may be identical or different, are chosen from a hydrogen atom, a linker arm Y and a $C_1$–$C_4$ alkyl radical; with the proviso that the compounds of formula (II) comprise only one linker arm Y per molecule.

14. The composition according to claim 13, wherein the nitrogenous groups are chosen from amino, mono($C_1$–$C_4$)alkylamino, di($C_1$–$C_4$)alkylamino, tri($C_1$–$C_4$)alkylamino, monohydroxy($C_1$–$C_4$)alkylamino, imidazolinium and ammonium radicals.

15. The composition according to claim 10, wherein the para-aminophenols are chosen from the compounds of formula (III):

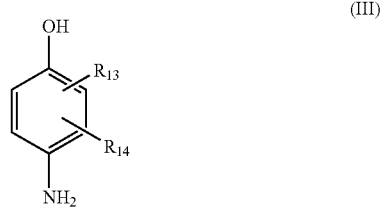

in which:

$R_{13}$ is chosen from a hydrogen atom, a halogen atom and a $C_1$–$C_4$ alkyl, $C_1$–$C_4$ monohydroxyalkyl, ($C_1$–$C_4$) alkoxy($C_1$–$C_4$)alkyl, $C_1$–$C_4$ aminoalkyl and hydroxy ($C_1$–$C_4$)alkylamino($C_1$–$C_4$)alkyl radical, $R_{14}$ is chosen from a hydrogen atom, a halogen atom and a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or ($C_1$–$C_4$)alkoxy($C_1$–$C_4$)alkyl radical.

16. The composition according to claim 10, wherein the heterocyclic bases are chosen from pyridine derivatives, pyrimidine derivatives and pyrazole derivatives.

17. The composition according to claim 8, wherein the at least one oxidation base is present in a concentration ranging from 0.0005% to 12% by weight relative to the total weight of the composition.

18. The composition according to claim 8, wherein the at least one coupler is chosen from meta-phenylenediamines, meta-aminophenols, meta-diphenols and heterocyclic couplers, and the acid-addition salts thereof.

19. The composition according to claim 8, wherein the at least one coupler is present in a concentration ranging from 0.0001% to 10% by weight relative to the total weight of the composition.

20. The composition according to claim 10, wherein the acid-addition salts of the oxidation bases are chosen from hydrochlorides, hydrobromides, sulfates, tartrates, lactates and acetates.

21. The composition according to claim 18, wherein the acid-addition salts of the couplers are chosen from meta-phenylenediamines, meta-aminophenols, meta-diphenols and heterocyclic couplers, and the acid-addition salts thereof.

22. The composition according to claim 1, further comprising at least one direct dye.

23. The composition according to claim 22, wherein the at least one direct dye is present in an amount ranging from 0.001% to 20% by weight relative to the total weight of the composition.

24. The composition according claim 1, further comprising at least one reducing agent or antioxidant, in an amount ranging from 0.05% to 3% by weight relative to the total weight of the composition.

25. The composition according to claim 1, further comprising at least one surfactant chosen from anionic, cationic, nonionic and amphoteric surfactants.

26. The composition according to claim 25, further comprising at least one anionic surfactant of oxyethylenated (C8–C30)alkyl ether carboxylic acid type.

27. The composition according to claim 25, further comprising at least one oxyalkylenated or monoglycerolated or polyglycerolated nonionic surfactant.

28. The composition according to claim 25, wherein the at least one surfactant comprises 0.01% to 40% by weight relative to the total weight of the composition.

29. The composition according to claim 1, further comprising at least one associative polymer chosen from nonionic, anionic, cationic and amphoteric associative polymers and present in an amount ranging from 0.01% to 10% by weight relative to the total weight of the composition.

30. The composition according to claim 1, further comprising at least one cationic or amphoteric polymer in an amount ranging from 0.01 % to 10% by weight relative to the total weight of the composition.

31. The composition according to claim 1, further comprising at least one unsaturated fatty alcohol in an amount ranging from 0.5% to 15% by weight relative to the total weight of the composition.

32. The composition according to claim 1, further comprising water and, at least one solvent chosen from linear or branched monoalcohols and diols comprising 2 to 10 carbon atoms; aromatic alcohols; glycols, glycol ethers, and diethylene glycol alkyl ethers; and mixtures thereof.

33. The composition according to claim 32, wherein the at least one solvent is present in an amount ranging from 0.5% to 20% by weight relative to the total weight of the composition.

34. The composition according to claim 1, wherein it is in the form of a liquid.

35. A ready-to-use composition for the oxidation dyeing of keratin fibers, comprising a mixture of an oxidizing composition comprising at least one oxidizing agent with a dye composition comprising, in a medium suitable for dyeing, at least one oxidation dye and at least one oxyethlyenated rapeseed fatty acid amide present in an amount greater than 5% by weight relative to the total weight of the composition.

36. A composition for oxidation dyeing wherein said keratin fibers are human hair.

37. The composition according to claim 35, wherein the at least one oxidizing agent is chosen from hydrogen peroxide, urea peroxide, alkali metal bromates or ferricyanides, persalts, redox enzymes, optionally in the presence of the respective donor or cofactor thereof.

38. The composition according to claim 37, wherein the at least one oxidizing agent is hydrogen peroxide.

39. The composition according to claim 38, wherein the at least one oxidizing agent is an aqueous hydrogen peroxide solution with a titre ranging from 1 to 40 volumes.

40. The composition according to claim 1, wherein the pH ranges from 3 to 12.

41. A process for dyeing keratin fibers comprising applying to the fibers at least one dye composition comprising, in a medium that is suitable for dyeing, at least one oxidation dye and greater than 5% by weight of the composition of at least one oxyethylenated rapeseed fatty acid amide, developing the color at alkaline, neutral or acidic pH with an oxidizing composition comprising, in a medium that is suitable for dyeing, at least one oxidizing agent, which is mixed just at the time of application with the dye composition or which is applied sequentially without intermediate rinsing.

42. A process for dyeing according to claim 41, wherein said keratin fibers are human hair.

43. A process according to claim 41, comprising preparing a ready-to-use composition extemporaneously at the time of application from the dye composition and the oxidizing composition, applying the ready to use composition to wet or dry keratin fibers, leaving the composition to act for a leave-in time ranging from 1 to 60 minutes, rinsing the fibers, then optionally washing them with shampoo, and then rinsing them again and drying them.

44. A process according to claim 43, wherein said leave-in time is from 10 to 45 minutes.

45. A multi-compartment kit for the dyeing of keratin fibers comprising at least one compartment comprising a dye composition comprising, in a medium that is suitable for dyeing, at least one oxidation dye and greater than 5% by weight of the composition of at least one oxyethylenated rapeseed fatty acid amide, and another compartment comprising an oxidizing composition comprising, in a medium that is suitable for dyeing, an oxidizing agent.

46. A kit according to claim 45, wherein said keratin fibers are human hair.

* * * * *